(12) United States Patent
Onami et al.

(10) Patent No.: US 7,917,300 B2
(45) Date of Patent: Mar. 29, 2011

(54) METHOD AND PROGRAM FOR PREDICTING GENE NETWORK

(75) Inventors: Shuichi Onami, Kanagawa (JP); Koji Kyoda, Kanagawa (JP)

(73) Assignees: Japan Science and Technology Agency, Saitama (JP); Keio University, Tokyo (JP)

( * ) Notice: Subject to any disclaimer, the term of this patent is extended or adjusted under 35 U.S.C. 154(b) by 1131 days.

(21) Appl. No.: 11/597,428

(22) PCT Filed: May 24, 2005

(86) PCT No.: PCT/JP2005/009448
§ 371 (c)(1),
(2), (4) Date: Nov. 22, 2006

(87) PCT Pub. No.: WO2005/114531
PCT Pub. Date: Dec. 1, 2005

(65) Prior Publication Data
US 2008/0015788 A1    Jan. 17, 2008

(30) Foreign Application Priority Data

May 24, 2004  (JP) .................................. 2004-153739

(51) Int. Cl.
*G06F 19/00* (2006.01)
(52) U.S. Cl. .......................................... 702/19; 702/20
(58) Field of Classification Search .................... None
See application file for complete search history.

(56) References Cited

U.S. PATENT DOCUMENTS

2002/0019705 A1*  2/2002  Kauffman et al. .............. 702/19
2004/0029154 A1   2/2004  Kyoda et al.

FOREIGN PATENT DOCUMENTS

JP          7-262019       10/1995
WO        WO 02/38749       5/2002

OTHER PUBLICATIONS

Morohashi et al. (Advances in Artificial Life: Proceedings of the 5th European Conference in Artificial Life, Sep. 13-17, 1999: pp. 477-486).*
Noda et al. (Genome Informatics Workshop, vol. 9, pp. 141-150; Japanese Society for Bioinformatics, Dec. 10-11, 1998).*
Written Opinion of the International Searching Authority, filing date May 24, 2005.
Kyoda et al., "A Gene Network Inference Method from Continuous-Value Gene Expression Data of Wild-Type and Mutants." Genome Informatics, vol. 11, pp. 196-204, (2000).
Masahiro Okamoto, "Development of the Inference System of Large Scale Genetic Networks." The Japanese Society for Artificial Intelligence, pp. 7-14, Nov. 13, 2000.
Kyoda et al."DBRF-MEGN Method: An Algorithm for Deducing Minimum Equivalent Gene Networks from Large-Scale Gene Expression Profiles of Gene Deletion Mutants." Bioinformatics vol. 20, No. 16, pp. 2662-2675, (May 27, 2004).

\* cited by examiner

*Primary Examiner* — Lori A Clow
(74) *Attorney, Agent, or Firm* — Dickstein Shapiro LLP

(57) ABSTRACT

A gene network is predicted which can prevent a decrease in the amount of basic data. A gene network is predicted by retrieving indirect causal relationships the presence of which cannot be explained on the basis of direct causal relationships and/or indirect causal relationships the presence of which can be explained on the basis of the direct causal relationships and supplementing a network comprising the direct causal relationships with the retrieved indirect causal relationships.

8 Claims, 26 Drawing Sheets

Fig. 10

|        | $x_0$ | $x_1$ | $x_2$ | $x_3$ |
|--------|-------|-------|-------|-------|
| wt     | 3.750 | 3.750 | 8.939 | 0.078 |
| $a_0^-$ | –    | 3.750 | 8.769 | 0.011 |
| $a_1^-$ | 3.750 | –    | 8.769 | 0.086 |
| $a_2^-$ | 3.750 | 3.750 | –    | 5.476 |
| $a_3^-$ | 3.750 | 3.750 | 8.939 | –    |

Fig. 11

|       | $a_0$ | $a_1$ | $a_2$ | $a_3$ |
|-------|-------|-------|-------|-------|
| $a_0$ |       |       | +     | +     |
| $a_1$ |       |       | +     |       |
| $a_2$ |       |       |       |       |
| $a_3$ |       |       |       | −     |

METHOD AND PROGRAM FOR PREDICTING GENE NETWORK

CLAIM FOR PRIORITY

The present specification embraces the contents described in the specification and/or drawings of Japanese Patent Application No. 2004-153739, on which the priority of the present application is based.

TECHNICAL FIELD

The present invention relates to a method and program for predicting a gene network, which is applicable to construction of a gene network on the basis of gene expression data or the like.

BACKGROUND ART

Owing to recent advances in the field of molecular biology, an enormous amount of gene information is now available. As a consequence, it is necessary to make efforts using computers to extract information from a rapidly increasing number of successively clarified sequence data or an enormous number of gene expression data. Development of various computer tools for homology screening, protein classification, gene pooling, and the like has been attracting attention so far.

In connection with these attempts, several but not so many examples of studies are known which relate to methods of inferring a gene regulation network (hereinafter referred to as a gene network) from gene expression data. Gene expression data can be obtained in either the form of time series data ("time series data" refers to data obtained by measurement of gene expression amounts of a subject group of genes over the course of time), or steady state data ("steady state data" refers to data obtained by measurement of gene expression amounts of a subject group of genes under a plurality of differing experimental conditions (for example, gene mutation, or administration of a medicament)).

A method of analyzing a time series can predict a network using various methods, for example, information theory, heredity algorithm or simulated annealing (Non-Patent Document 1). However, an approach based on analysis of a time series requires that experimental results are obtained at very short intervals without experimental noise. This is very difficult to achieve with current techniques.

On the other hand, a number of methods of analyzing a steady state data have already been proposed. The steady state data can be obtained by mutating a specific gene activity, for example, by causing deletion or over-expression of a gene. Deletion is presently being performed on a large scale by the Yeast Genome Deletion Consortium and the like, and as a result, deletion-type expression profiles for various genes will become readily available in the near future (Non-Patent Document 2).

The present inventors have developed a new method and program for predicting a gene network, which predicts a gene network without simplifying (binarizing) the gene expression amount using, as basic data, a gene expression profile (detected values) obtained by inducing mutation (Patent Document 1). With this method, one of a plurality of genes is expressed under two conditions and the expression amount of this gene is detected for each of the conditions. At this time, the expression amount of each of the other genes is detected for each of the conditions. The difference among the detected values obtained is then determined and used as an indicator to derive the causal relationship between the one of the genes and the others.

Patent Document 1 also discloses a method for predicting a gene network which method detects and removes an indirect causal relationship (expressed as a "redundant causal relationship" in Patent Document 1) from a given gene network.

Non-Patent Document 1: Liang, S. et al., Proc. Pacific Symp. Biocomputing '98, World Scientific, 18-29, 1998.; Morohashi, M. and Kitano, H., Proc. 5th Euro. Conf. Artificial Life, Springer, 477-486, 1999.; Mjolsness, E., et al., Tech. Rept. JPL-ICTR-99-4, Jet Propulsion Lab., NASA, 1999.

Non-Patent Document 2: Winzeler, E. A. et al., Science, 285 (5429): 901-906, 1999.

Patent Document 1: WO 2002/038749

DISCLOSURE OF THE INVENTION

However, if for example, the method of predicting a gene network disclosed in Patent Document 1 is applied to predict a gene network from which its indirect causal relationship has been removed, all existence of the indirect causal relationships may not be explained on the basis of the predicted gene network. That is, if the gene network from which its indirect causal relationship has been removed is predicted, this disadvantageously corresponds to the prediction of the gene network from which a part of the basic data has been lost. Here, the basic data reflects the actual gene expression control relationship in a living organism. Thus, losing a part of the basic data prevents the predicted gene network from reflecting the actual gene expression control relationship.

Thus, as a result of examinations for solving the above problems, the inventors have found that a gene network free from the loss of data amount can be predicted by retrieving, from causal relationships detected as indirect causal relationships, indirect causal relationships whose presence cannot be explained on the basis of non-indirect causal relationships (hereinafter referred to as a direct causal relationship) and/or indirect causal relationships whose presence can be explained on the basis of the direct causal relationships, and supplementing a network consisting of the direct causal relationships with the retrieved indirect causal relationships. The inventors have thus completed the present invention.

That is, the present invention embraces the following.

(1) A method of predicting a gene network comprising indirect causal relationships and direct causal relationship, in which a control relationship between a pair of genes is defined as a causal relationship and the causal relationship between the pair of genes is defined as a direct causal relationship if the pair of genes does not have a further causal relationship with another common gene, and in which the causal relationship between the pair of genes is defined as a direct causal relationship if the pair of genes has a further causal relationship with another common gene and if the presence of the causal relationship between the pair of genes cannot be explained by the causal relationship between the pair of genes and the another gene, and in which the causal relationship between the pair of genes is defined as an indirect causal relationship if the pair of genes has a further causal relationship with another common gene and if the presence of the causal relationship between the pair of genes can be explained by the causal relationship between the pair of genes and the another gene, the method comprising:

a step A of retrieving indirect causal relationships from a set of causal relationships relating to at least three genes;

a step B of retrieving, from the indirect causal relationships retrieved in the step A, indirect causal relationships whose presence can be explained on the basis of the direct causal relationships, and subsequently retrieving the indirect causal relationships whose presence can be explained on the basis of the direct causal relationships and/or the indirect causal relationships whose presence can be explained on the basis of the direct causal relationships;

a step C of retrieving, from the indirect causal relationships retrieved in the step A from which the indirect causal relationships retrieved in the step B are excluded, a minimum number of indirect causal relationships that can explain the presence of all the indirect causal relationships in cooperation with the direct causal relationships and the indirect causal relationships retrieved in the step B; and a step D of excluding the indirect causal relationships from the set of causal relationships and adding the minimum number of indirect causal relationships retrieved in the step C to the resulting set of causal relationships to calculate a set of causal relationships, and predicting a gene network consisting of the calculated set of causal relationships.

(2) The method of predicting a gene network set forth in (1), wherein in the step A, provided that when a causal relationship between a gene A and a gene B, a causal relationship between the gene A and a gene C, and a causal relationship between the gene C and the gene B is present among the gene A, the gene B and the gene C and the causal relationship between the gene A and the gene B is a positive causal relationship, the causal relationship between the gene A and the gene C and the causal relationship between the gene C and the gene B contain an even number of causal relationships, or provided that when the causal relationship between the gene A and the gene B is a negative causal relationship, the causal relationship between the gene A and the gene C and the causal relationship between the gene C and the gene B contain an odd number of negative causal relationships, the causal relationship between the gene A and the gene B is defined as an indirect causal relationship.

(3) The method of predicting a gene network set forth in (1), wherein the step C includes:

a step E of defining the indirect causal relationships retrieved in the step A except the indirect causal relationships retrieved in the step B, as unexplainable indirect causal relationships, and retrieving, as minor unexplainable indirect causal relationships, those of the unexplainable indirect causal relationships which can explain none of the unexplainable indirect causal relationships in cooperation with one of the causal relationships included in the set of causal relationships on which the retrieval has been executed in the step A;

a step F of repeating a process of adding indirect causal relationships included in the unexplainable indirect causal relationships except the minor unexplainable indirect causal relationships to the set of minor unexplainable indirect causal relationships, wherein the added indirect causal relationships can explain only the minor unexplainable indirect causal relationships among the unexplainable indirect causal relationships in cooperation with one of the causal relationships included in the set of causal relationships on which the retrieval has been executed in the step A, until there remains no indirect causal relationships to be added;

a step G of dividing a set of unexplainable indirect causal relationships not included in the set of indirect causal relationships detected in the step F, into groups; and a step H of retrieving a minimum number of indirect causal relationships for each of the groups formed in the step G, on the basis of the indirect causal relationships included in the group.

(4) The method of predicting a gene network set forth in (3), wherein in the step G, the group division is carried out so that a minimum number of indirect causal relationships included in a particular group explains only the indirect causal relationships included in the group.

(5) A program for predicting a gene network comprising indirect causal relationships and direct causal relationship, in which a control relationship between a pair of genes is defined as a causal relationship and the causal relationship between the pair of genes is defined as a direct causal relationship if the pair of genes does not have a further causal relationship with another common gene, and in which the causal relationship between the pair of genes is defined as a direct causal relationship if the pair of genes has a further causal relationship with another common gene and if the presence of the causal relationship between the pair of genes cannot be explained by the causal relationship between the pair of genes and the another gene, and in which the causal relationship between the pair of genes is defined as an indirect causal relationship if the pair of genes has a further causal relationship with another common gene and if the presence of the causal relationship between the pair of genes can be explained by the causal relationship between the pair of genes and the another gene, the program, in estimating the gene network, allowing a computer to execute:

a step A of using retrieval means to retrieve indirect causal relationships from a set of data on causal relationships relating to at least three genes;

a step B of using the retrieval means to retrieve, from the set of data on the indirect causal relationships retrieved in the step A, indirect causal relationships whose presence can be explained on the basis of the direct causal relationships, and subsequently using the retrieval means to retrieve indirect causal relationships whose presence can be explained on the basis of a set of data on direct causal relationships and/or the indirect causal relationships whose presence can be explained on the basis of the direct causal relationships;

a step C of using the retrieval means to retrieve a minimum number of indirect causal relationships that can explain the presence of all the indirect causal relationships in cooperation with the direct causal relationships and the indirect causal relationships retrieved in the step B, from a set of data on indirect causal relationships calculated by using calculation means to exclude the data on the indirect causal relationships retrieved in the step B from the set of data on the indirect causal relationships retrieved in the step A; and a step D of using the calculation means to exclude the data on the indirect causal relationships from the set of data on causal relationships and using the calculation means to add the minimum number of indirect causal relationships retrieved in the step C to the resulting set of data on causal relationships to calculate a set of data on causal relationships, and using output means to output a gene network consisting of the calculated set of data on causal relationships.

(6) The program for predicting a gene network set forth in (5), wherein in the step A, if the following condition is met: when a causal relationship between a gene A and a gene B, a causal relationship between the gene A and a gene C, and a causal relationship between the gene C and the gene B is present among the gene A, the gene B and the gene C and the causal relationship between the gene A and the gene B is a positive causal relationship, the causal relationship between the gene A and the gene C and the causal relationship between the gene C and the gene B contain an even number of negative causal relationships, or if the following condition is met: when the causal relationship between the gene A and the gene B is a negative causal relationship, the causal relationship between the gene A and the gene C and the causal relationship between the gene C and the gene B contain an odd number of negative causal relationships, the causal relationship between the gene A and the gene B is retrieved as an indirect causal relationship.

(7) The program for predicting a gene network set forth in (5), wherein the step C includes:

a step E of defining the set of data on the indirect causal relationships retrieved in the step A from which the indirect causal relationships retrieved in the step B are excluded using the calculation means, as a set of data on unexplainable indirect causal relationships, and using the retrieval means to retrieve, from the resulting set of data on the unexplainable indirect causal relationships, indirect causal relationships that can explain none of the unexplainable indirect causal relationships in cooperation with one of the causal relationships included in the set of data on causal relationships on which the retrieval has been executed in the step A, as the minor unexplainable indirect causal relationship;

a step F of repeating a process of using the calculation means to add indirect causal relationships included in the unexplainable indirect causal relationships from which the minor unexplainable indirect causal relationships are excluded using the calculation means to the set of minor unexplainable indirect causal relationships, wherein the added indirect causal relationships can explain only the minor unexplainable indirect causal relationships among the unexplainable indirect causal relationships in cooperation with one of the causal relationships included in the set of causal relationships on which the retrieval has been executed in the step A using the retrieval means, until there remains no indirect causal relationships to be added;

a step G of using the calculation means to divide a set of data on unexplainable indirect causal relationships not included in the set of indirect causal relationships detected in the step F, into groups; and a step H of using the retrieval means to retrieve a minimum number of indirect causal relationships for each of the groups formed in the step G, on the basis of the indirect causal relationships included in the group.

(8) The program for predicting a gene network set forth in (7), wherein in the step G, the calculation means carries out the group division so that a minimum number of indirect causal relationships included in a particular group explains only the indirect causal relationships included in the group.

EFFECTS OF THE PRESENT INVENTION

The present invention can provide a method and program for predicting a gene network, which, in predicting a gene network using gene expression data or the like as basic data, prevents the amount of the basic data from being lost.

BRIEF DESCRIPTION OF THE DRAWINGS

FIG. 10 is a diagram showing an example of data in which the expression amount $X_n$ of a gene $a_n$ (n=0,1,2,3 . . . ) is accumulated for each disrupted strain $a_n^-$ of the gene $a_n$;

FIG. 11 is a diagram showing an example of a database showing the expression control relationships among genes;

EXPLANATION OF REFERENCE NUMERALS

101 . . . CPU (control means), 102 . . . ROM, 103 . . . RAM, 104 . . . input means, 105 . . . transmission/reception means, 106 . . . output means, 107 . . . hard disk drive (HDD), 108 . . . CD-ROM drive, 110 . . . public database, 111 . . . retrieval means, 112 . . . calculation means

BEST MODE FOR CARRYING OUT THE INVENTION

With reference to the drawings, a detailed description will be given below of a method and program for predicting a gene network.

1. Concepts of the Invention

A prediction program according to the present invention predicts a gene network by excluding indirect causal relationships from a gene network (hereinafter referred to as an original network) comprising direct causal relationships and indirect causal relationships and constructed on the basis of the gene expression data or the like and adding, to the resulting gene network, a minimum number of indirect causal relationships that allow the reproduction of gene expression data or the like.

Here, the causal relationship means the control relationship between a pair of genes. The control relationship means a relationship in which one of the genes inhibits or promotes the expression of the other (gene expression control relationship), a relationship in which one of two gene products activates or inactivates the other, or the like. For example, for the genes A and B, if the expression amount of the gene b observed when the gene a is mutated (for example, the gene a is deleted) is significantly different from that of the gene b observed when the gene a is not mutated (for example, the gene a is of a wild type) or the difference in expression amount exceeds a threshold, there is a causal relationship between the genes a and b.

Further, the causal relationship may be defined as a positively controlling causal relationship or a negatively controlling causal relationship. That is, the relationship in which the gene a promotes the expression of the gene b may be defined as a positive causal relationship. The relationship in which the gene a inhibits the expression of the gene b may be defined as a negative causal relationship. Alternatively, the relationship in which a gene a product activates a gene b product may be defined as a positive causal relationship. The relationship in which the gene a product inactivates the gene b product may be defined as a negative causal relationship.

Figure 1:
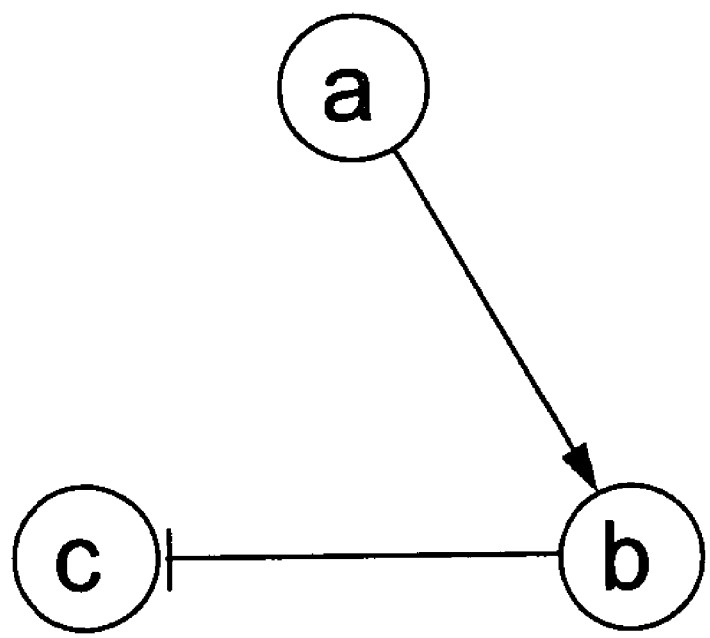
FIG. 1 is a diagram showing a simplified symbolic directed graph illustrating a gene network.

Here, the gene network may be replaced with a diagram called a "symbolic directed graph" for convenience of description (FIG. 1). In FIG. 1, the alphabets denote genes, and the arrow (→) means the causal relationship in which the gene a positively controls the gene b. The T-shaped arrow (⊣) means the causal relationship in which the gene b negatively controls the gene c. The individual arrows are called "edges" in the present invention.

On the other hand, the indirect causal relationship means a causal relationship between a gene a and gene b in which the genes a and b have a causal relationship and in which the genes a and b have a further causal relationship with another common gene (hereinafter referred to as a gene c) and in which the causal relationship between the gene a and the gene b can be explained by the causal relationship between the gene a and the gene c and the causal relationship between the gene c and the gene b.

Here, the "relationship that can be explained by the causal relationship between the gene a and the gene c and the causal relationship between the gene c and the gene b" enables the causal relationship between the gene a and the gene b to be consistently explained on the basis of the causal relationship between the gene a and the gene c and the causal relationship between the gene c and the gene b in terms of the gene expression control relationship or the control relationship such as signal transmissions, and includes the possibility that the action of the gene a on the gene b is indirect.

For example, the indirect causal relationship can occur if the expression analysis of the genes b and c with the gene a inactivated results in the recognition that the gene a is able to indirectly activate the gene c, even though the gene a is actually unable to activate the gene b.

For convenience, the symbolic directed graph shown in FIG. 2 will be described. If the gene a and gene b have a causal relationship (broken line) in which the gene a positively controls the gene b and there are further causal relationships between the gene a and the gene c and between the gene c and the gene b, when the causal relationship between the gene a and the gene c and the causal relationship between the gene c and the gene b contain an even number of negatively controlling causal relationships, the "causal relationship in which the gene a positively controls the gene b" is defined as an indirect causal relationship. Further, as shown in FIG. 3, if the genes a and b have a causal relationship (broken line) in which the gene a negatively controls the gene b and there are further causal relationships between the gene a and the gene c and between the gene c and the gene b, when the causal relationship between the gene a and the gene c and the causal relationship between the gene c and the gene b contain an odd number of negatively controlling causal relationships, the "causal relationship in which the gene a negatively controls the gene b" is defined as a indirect causal relationship.

On the other hand, the direct causal relationship means all the causal relationships other than the above indirect causal relationships. That is, the direct causal relationship means a causal relationship in which the causal relationship between the gene a and the gene b cannot be explained by the causal relationship between the gene a and the gene c and the causal relationship between the gene c and the gene b. In other words, in the direct causal relationship, the causal relationship between the gene a and the gene b cannot be consistently explained on the basis of the causal relationship between the gene a and the gene c and the causal relationship between the gene c and the gene b in terms of the gene expression control relationship or the control relationship such as signal transmissions. The direct causal relationship allows the action of the gene a on the gene b to be reasonably determined to be direct.

Figure 4:
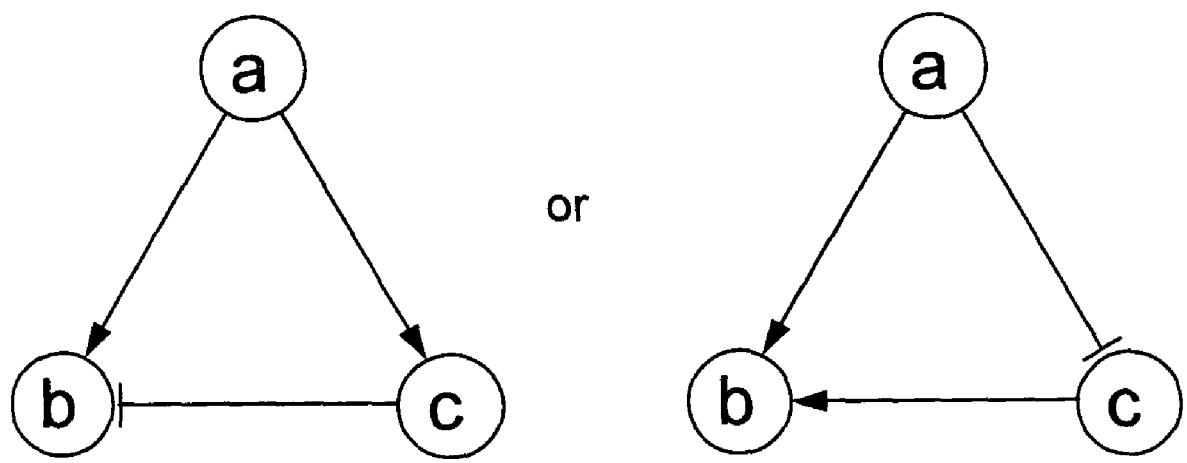
FIG. 4 is a diagram showing a symbolic directed graph illustrating a gene network comprising the genes a, b, and c and in which the genes a and b have a direct causal relationship that is a causal relationship in which the gene a positively controls the gene b.
Figure 5:
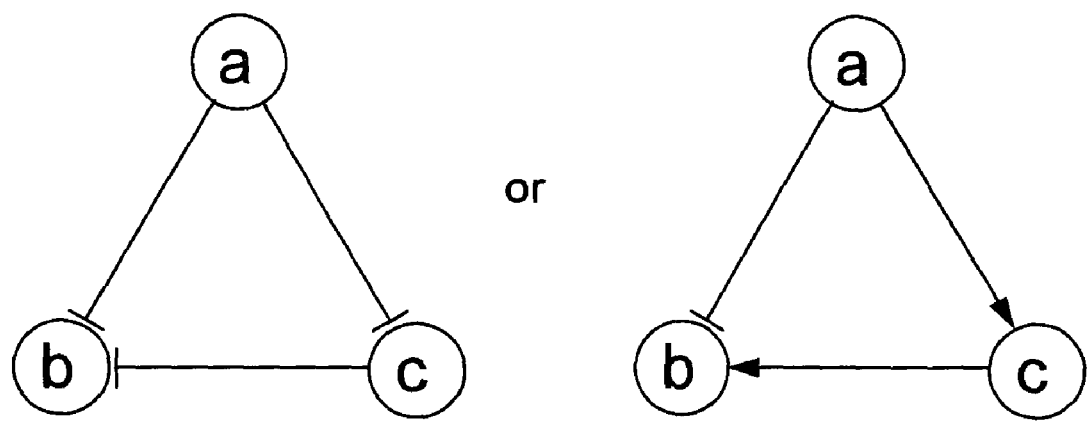
FIG. 5 is a diagram showing a symbolic directed graph illustrating a gene network comprising the genes a, b, and c and in which the genes a and b have a direct causal relationship that is a causal relationship in which the gene a negatively controls the gene b.

For convenience, the symbolic directed graph shown in FIG. 4 will be described. If the genes a and b have a causal relationship in which the gene a positively controls the gene b and there are further causal relationships between the gene a and the gene c and between the gene c and the gene b, when the causal relationship between the gene a and the gene c and the causal relationship between the gene c and the gene b contain an odd number of negatively controlling causal relationships, the "causal relationship in which the gene a positively controls the gene b" is defined as a direct causal relationship. Further, as shown in FIG. 5, if the genes a and b have a causal relationship in which the gene a negatively controls the gene b and there are further causal relationships between the gene a and the gene c and between the gene c and the gene b, when the causal relationship between the gene a and the gene c and the causal relationship between the gene c and the gene b contain an even number of negatively controlling causal relationships, the "causal relationship in which the gene a negatively controls the gene b" is defined as a direct causal relationship. Moreover, if the genes a and b have a causal relationship and whatever the gene c is, the gene a does not have a causal relationship with the gene c and the gene c does not have a causal relationship with the gene b, the "causal relationship in which the gene a positively or negatively controls the gene b" is defined as a direct causal relationship. That is, in this case, if the gene a and gene b do not have a causal relationship with another common gene, the "causal relationship in which the gene a positively or negatively controls the gene b" is defined as a direct causal relationship.

A minimum number of causal relationships that allow gene expression data or the like to be reproduced (hereinafter sometimes referred to MEGN (Minimum Equivalent Gene Network)) mean a minimum number of causal relationships added to a network obtained by excluding the indirect causal relationship from an original network so as to reconstruct the original network, that is, to enable the presence of all the excluded indirect causal relationships to be explained.

Figure 6:
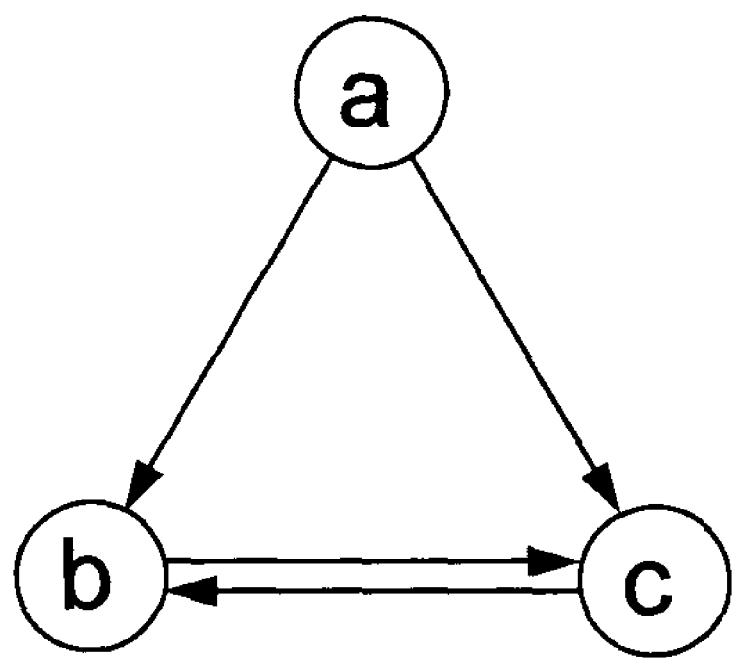
FIG. 6 is a diagram showing, as a symbolic directed graph, an example of a gene network comprising the genes a, b, and c.
Figure 7:
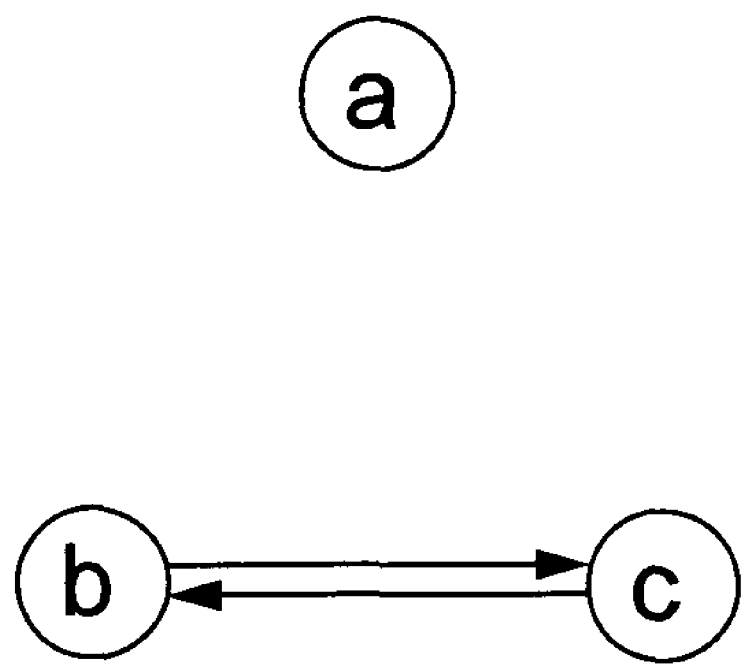
FIG. 7 is a diagram showing a gene network constructed by excluding the indirect causal relationships from the gene network shown in FIG. 6.

For convenience of description, a simplified original network is assumed to comprise the causal relationship in which the gene a positively controls the gene b, the causal relationship in which the gene a positively controls the gene c, the causal relationship in which the gene b positively controls the gene c, and the causal relationship in which the gene c positively controls the gene b, as shown in FIG. 6. In the gene network shown in FIG. 6, according to the above definition of the indirect causal relationship, the causal relationship in which the gene a positively controls the gene b and the causal relationship in which the gene a positively controls the gene c are indirect causal relationships. In this case, the gene network constructed by excluding the indirect causal relationships from the original network contains only the direct causal relationships between the gene b and the gene c as shown in FIG. 7. The gene network shown in FIG. 7 cannot explain the presence of the indirect causal relationship between the gene a and the gene b or the indirect causal relationship between the gene a and the gene c. The amount of information in this network is undesirably smaller than that in the original network predicted on the basis of gene expression data or the like.

Thus, the information being lost in the gene network shown in FIG. 7, that is, either the indirect causal relationship between the gene a and the gene b or the indirect causal relationship between the gene a and the gene c, is defined as a "minimum number of causal relationships that allow gene expression data or the like to be reproduced".

Figure 8:
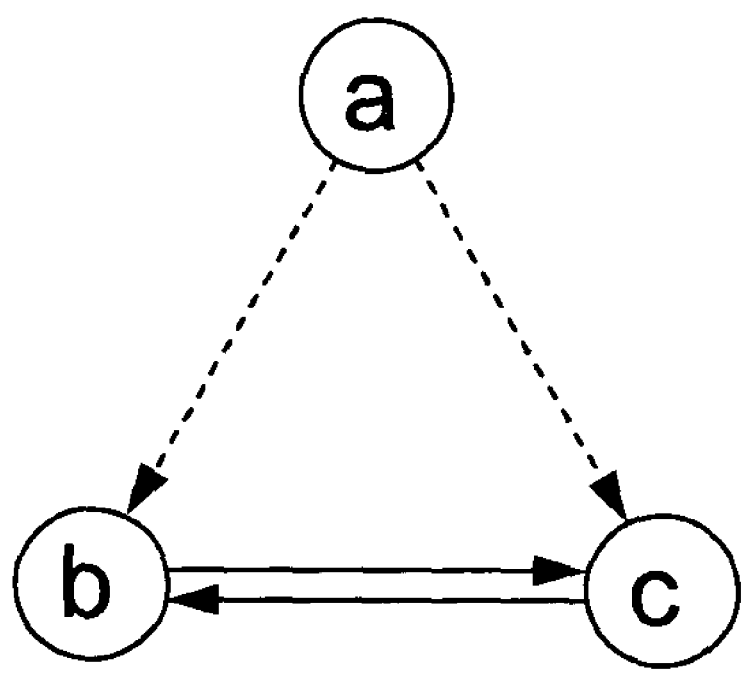
FIG. 8 is a diagram showing a gene network constructed by adding a minimum number of causal relationships that allow gene expression data or the like to be reproduced, to the gene network shown in FIG. 7.

The method and program for predicting a gene network according to the present invention predicts a gene network constructed by retrieving the "minimum number of causal relationships that allow gene expression data or the like to be reproduced" as described above, from the original network and adding the "minimum number of causal relationships that allow gene expression data or the like to be reproduced" to the original network from which the indirect causal relationships are excluded. For the gene network shown in FIG. 7, as shown in FIG. 8, a gene network is predicted to which one of the two causal relationships shown by broken lines in FIG. 8 has been added as a minimum number of causal relationships.

2. Prediction Program According to the Invention

Description will be given of a program for predicting a gene network according to the present invention. The present program allows a computer to implement the information processing described in "1. Concepts of the Invention", described above. Description will be given below of, as an example of a causal relationship, the control relationship (gene expression control relationship) in which one of two genes inhibits or promotes the expression of the other. However, the present program is applicable even if the causal relationship means a relationship in which one of the gene products activates or inactivates the other.

Figure 9:
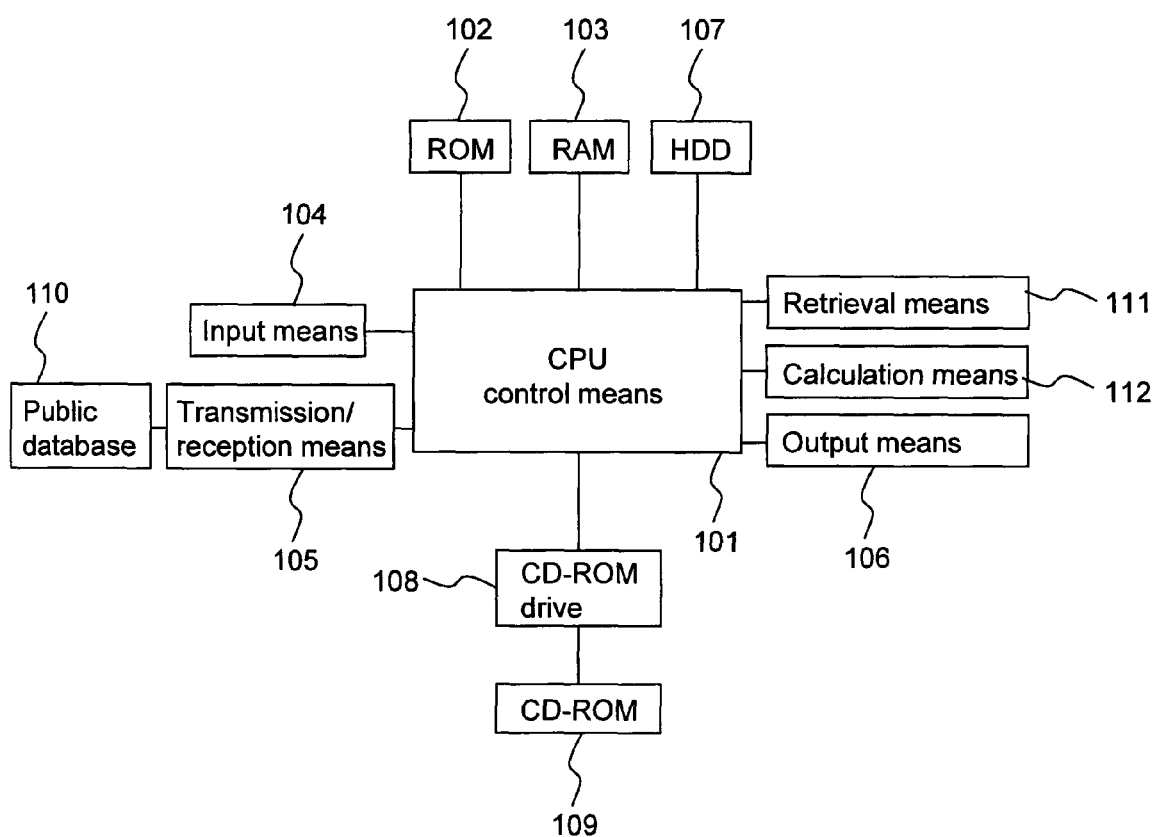
FIG. 9 is a diagram showing an example of configuration of a computer in which a prediction program according to the present invention is installed.

A computer comprises a CPU 101 (control means), a ROM 102, a RAM 103, input means 104, transmission/reception means 105, output means 106, a hard disk drive (HDD) 107, and a CD-ROM drive 108, for example, as shown in FIG. 9. The computer also comprises retrieval means 111 for retrieving data recorded in the ROM 102, the RAM 103, the HDD 107, a public database 110, and the like, and calculating means 112 for executing an addition or subtraction process on data retrieved by the retrieval means 111 or data input via the input means 104.

Here, the present prediction program is stored in, for example, the ROM 102, RAM 103, and HDD 107. The CPU 101 then drivingly control the above hardware of the computer in accordance with the present program to execute the information processing described in "1. Concepts of the Invention" to predict the gene network.

The CPU 101 controls the whole gene network system to execute a gene network prediction process described below. The RAM 103 temporarily stores data required to execute the gene network prediction process. The input means 104 is a keyboard, a mouse, and the like and is operated to, for example, input conditions required to execute the gene network prediction process. The transmission/reception means 105 executes a process of transmitting or receiving data to or from the public database 110 or the like via a communication line on the basis of instructions from the CPU 101. The output means 106 executes a process of displaying the expression amounts of genes, various conditions input by the input means 104, the base sequences of genes, and network prediction results, on the basis of instructions from the CPU 101. The output means 106 may be, for example, a computer display or a printer. The HDD 107 stores the gene network prediction program, gene expression amounts, base sequences, and the like. The HDD 107 reads and stores the stored programs or data in, for example, the RAM 103 on the basis of instructions from the CPU 101. The CD-ROM drive 108 reads the program, data or the like from the gene network prediction program or expression amounts stored in the CD-ROM 109 and stores it in, for example, the RAM 103.

The CPU 101 supplies the output means 106 with the data received from the input means 104 or the like and execute a process of predicting the gene network on the basis of the data received from the database.

Here, the program for predicting a gene network allows the computer to function as the means (i) to (iv) described below.

(i) Means (also referred to as an "indirect causal relationship retrieval engine") for retrieving indirect causal relationships from a set of causal relationships comprising direct causal relationships and indirect causal relationships.

(ii) Means (also referred to as an "explainable indirect causal relationship retrieval engine") for retrieving, from the indirect causal relationships retrieved by the indirect causal relationship retrieval engine, indirect causal relationships whose presence can be explained on the basis of the direct causal relationships, and subsequently retrieving the indirect causal relationships whose presence can be explained on the basis of the direct causal relationships and/or the indirect causal relationships whose presence can be explained on the basis of the direct causal relationships.

(iii) Means (also referred to as a "minimum number relationship retrieval engine") for retrieving, from the indirect causal relationships retrieved by the indirect causal relationship retrieval engine from which the indirect causal relationships retrieved by the explainable indirect causal relationship retrieval engine are excluded, a minimum number of indirect causal relationships that can explain the presence of all the indirect causal relationships in cooperation with the direct causal relationships and the indirect causal relationships retrieved by the explainable indirect causal relationship retrieval engine.

(iv) Means (also referred to as a "prediction engine") for excluding the indirect causal relationships from the set of causal relationships and adding the minimum number of indirect causal relationships retrieved by the minimum number relationships retrieval engine to the resulting set of causal relationships to calculate a set of causal relationships, and predicting a gene network comprising the calculated set of causal relationships.

(i) Indirect Causal Relationship Retrieval Engine

The indirect causal relationship retrieval engine retrieves indirect causal relationships from an original network predicted on the basis of gene expression data or the like. Here, the original network may be provided by a method disclosed in, for example, WO 2002/038749 or any other method. In the description below, by way of example, description will be given of prediction of an original network to which the method and program disclosed in WO 2002/038749.

The program for predicting the original network allows the computer to function as means (a) to (c) described below.

(a) Means (also referred to as a "detection engine") for, when the expression amount of one of the genes is set for two conditions, detecting the expression levels (expression amounts) of the other.

(b) Means (also referred to as a "comparison engine") for comparing detected values obtained with each other to determine the difference.

(c) Means (also referred to as a "causal relationship creation engine") for using the difference as an indicator to determine the causal relationship between the one of the genes and the other.

(a) Detection Engine

The detection engine means for detecting data (basic data) on which the control relationship between a pair of genes is based. For example, gene expressions can be detected by using or applying a DNA microarray, an oligonulcleotide chip, an RT-PCR, continuous analysis of gene expressions, steady state expression levels, proteomics, etc. That is, the detection engine enables the detection results to be input to the computer as gene expression data (expression amounts). The gene expression data is referred to as a detected value in the present invention.

The detected value may be an absolute value or a relative value. Further, values may be obtained from not only experimentally obtained data but also from literature, gene databases, or the like. For example, in respect of expression amounts obtained from a DNA microarray, intensity of fluorescence emanating from the microarray can be measured, and this fluorescence intensity can be converted to numerical values. Specific examples of a database include a database usable via the Internet, specifically, GenBank, DDBJ, EMBL, and NCI60.

Gene expression data detected by the detection engine can be expressed as the expression amount $X_n$ of a gene $a_n$ (n=0, 1,2,3 . . . ) accumulated for each disrupted strain $a_n^-$ of the gene $a_n$, for example, as shown in FIG. 10. wt denotes a wild type.

(b) Comparison Engine

The comparison engine calculates and accumulates information on the difference in expression levels of a subject gene observed in the case of the gene expression amount of one of the genes set for two conditions and information on the function (for example, activation or inhibition) between these genes. The setting of the two conditions for the gene expression amount includes the mutation of a gene, which means the loss of functions of or the over-expression of the original gene caused by deletion, substitution, or addition of base sequences. The mutation also includes disruption of a gene. That is, the two conditions for the gene expression amount can be defined as the gene expression amount of the wild type and the gene expression amount of a disrupted or over-expressed strain of a predetermined gene.

More specifically, when it is assumed that the detection engine detects the data shown in FIG. 10, the comparison engine calculates the difference between the expression amount of a predetermined gene of the wild type wt and the expression amount of that gene in each disrupted strain. That is, the difference between the expression amount of a gene a1 in a disrupted strain $a_0^-$ and the expression amount of the gene $a_1$ of the wild type is zero (3.750−3.750=0). The difference between the expression amount of a gene $a_2$ in the disrupted strain $a_0^-$ and the expression amount of the gene $a_2$ of the wild type is −0.17 (8.769−8.939=−0.17). Moreover, the difference between the expression amount of a gene $a_3$ in the disrupted strain $a_0^-$ and the expression amount of the gene $a_3$ of the wild type is −0.067 (0.011−0.078=−0.067). In the comparison engine, a calculation circuit can calculate the difference value between the detected values obtained by the detection engine.

The thus calculated difference value data is stored in storage means such as the ROM 102, RAM 103, or HDD 107 in association with code data indicating the types of disrupted strains or the types of disrupted genes in the disrupted strains and code data indicating the types of genes the difference between which is determined.

(c) Causal Relationship Creation Engine

The causal relationship creation engine is means for deriving the causal relationship between the pair of genes compared by the comparison engine, on the basis of the expression amount difference value data obtained by the comparison engine, and then predicting the original network. For example, in the case of examining the causal relationship between the gene a and the gene b, this means determines whether the gene a activates or inhibits the gene b (that is, the genes a and b have a causal relationship) or is unrelated with the gene b (that is, the genes a and b do not have any causal relationship) depending on the level of the difference between the expression amount of the gene b observed with the gene a mutated and the expression amount of the gene b observed with the gene a not mutated (when the gene a is of the wild type).

Specifically, the causal relationship creation engine first reads the difference value data accumulated by the comparison engine and compares a predetermined threshold with the difference value data. If the difference value data exceeds the threshold, the causal relationship creation engine determines from the code data associated with the difference data that there is a causal relationship between the disrupted gene in the disrupted strain and the gene that is subject to be determined the difference.

For example, if the difference value data does not exceed the threshold, the engine can determine that the disrupted gene in the disrupted strain indicated by the code data associated with the difference value data has not activated the gene that is subject to be determined the difference or the disrupted gene is unrelated with the latter gene. On the other hand, if the difference value data exceeds the threshold, the engine can determine that the disrupted gene in the disrupted strain indicated by the code data associated with the difference value data has activated or inhibited the gene that is subject to be determined the difference. The threshold can be appropriately set according to the target gene for the prediction of the network. However, the threshold is preferably set and adopted on the basis of a criterion such that an error testing results in, for example, a significant difference risk of at most 0.01.

More specifically, if the detection engine detects the data shown in FIG. 10, the causal relationship creation engine determines that the gene $a_0$ is unrelated with the gene $a_1$, that is, has no causal relationship with the gene $a_1$, because the difference in expression amount between the gene $a_1$ in the disrupted strain $a_0^-$ and the gene $a_1$ of the wild type is zero (3.750−3.750=0), as described above. Further, the causal relationship creation engine can predict that the gene $a_0$ activates the gene $a_2$, because the difference in expression amount between the gene $a_2$ in the disrupted strain $a_0^-$ and the gene $a_2$ of the wild type is 0.17 (8.769−9.939=0.17), provided that the threshold is neglected. Moreover, the causal relationship creation engine can predict that the gene $a_0$ activates the gene $a_3$, because the difference in expression amount between the gene $a_3$ in the disrupted strain $a_0^-$ and the gene $a_3$ of the wild type is 0.067 (0.011−0.078=−0.067).

Figure 11:
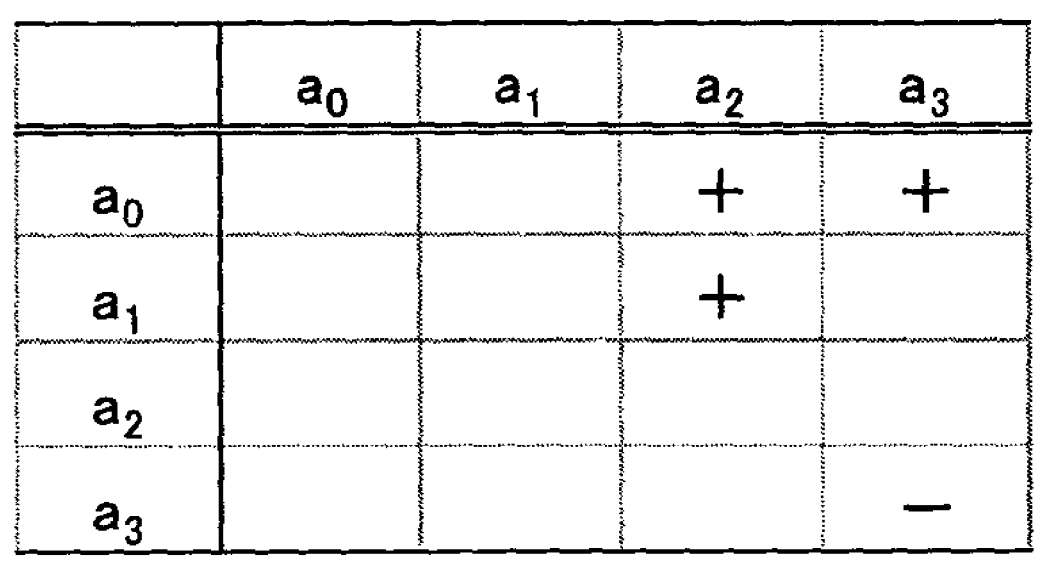
Figure 12:
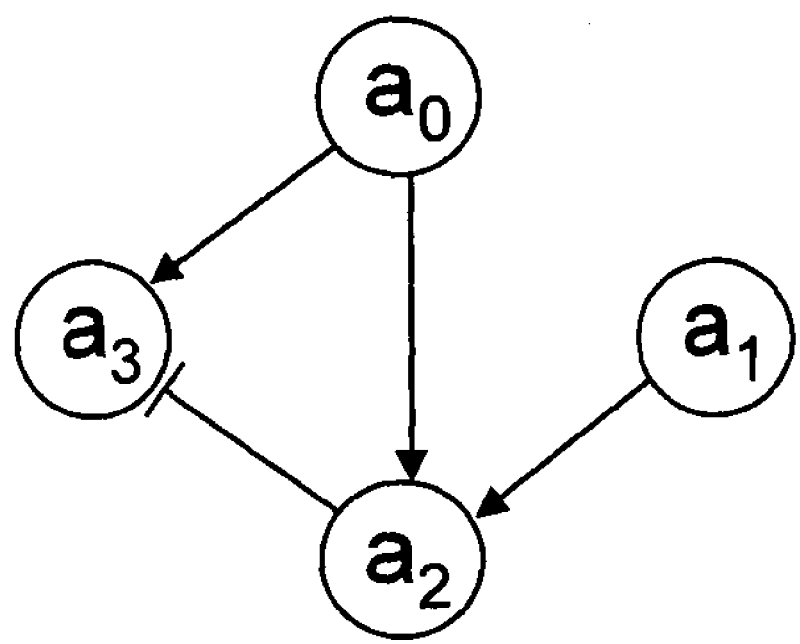
FIG. 12 is a diagram showing, as a symbolic directed graph, a gene network constructed using the data shown in FIGS. 10 and 11.

Consequently, the causal relationship creation engine enables, for example, such a relational database as shown in FIG. 11 to be constructed on the basis of the data shown in FIG. 10. In FIG. 11, "+" means activation and "−" means inhibition. Further, the causal relationship creation engine enables, for example, such a symbolic directed graph as shown in FIG. 12 to be constructed on the basis of the data shown in FIG. 10; the symbolic directed graph has the genes $a_0$ to $a_3$ as nodes.

Table 1 shows the relationship between the deletion or over-expression of the gene a and an increase or decrease in the expression level of the gene b. The calculation amount of this comparison process is $O(n^2)$.

TABLE 1

Relationship with a Rise or Fall in the Expression Level of the Gene

| | | Gene b expression level | |
|---|---|---|---|
| | | Increase | Decrease |
| Gene a | Deletion | a −| b | a → b |
| | Over-expression | a → b | a −| b |

Using the gene expression data detected by the detection engine, thus, the causal relationship creation engine can predict the original network as such a database as shown in FIG. 11 or such a symbolic directed graph as shown in FIG. 12. A set of causal relationships included in the original network is hereinafter referred to as an ET.

An indirect causal relationship retrieval engine retrieves indirect causal relationships from the original network predicted as described above or by another method.

The subject original network may have indirect causal relationships and direct causal relationships. However, the indirect causal relationship depends only on the parity of number of negative regulations involved in the edge route (Thieffry, D., and Thomas, R., Proc. Pacific Symp. Bio-computing '98, World Scientific, 77-78, 1998).

The indirect causal relationship retrieval engine retrieves indirect causal relationships included in the original network. The method for retrieving indirect causal relationships is not particularly limited. For example, the retrieval can be executed by a modified Warshall's algorithm for the field of graph theory (Gross, J., and Yellen, J., CRC Press, 1999).

Figure 13:
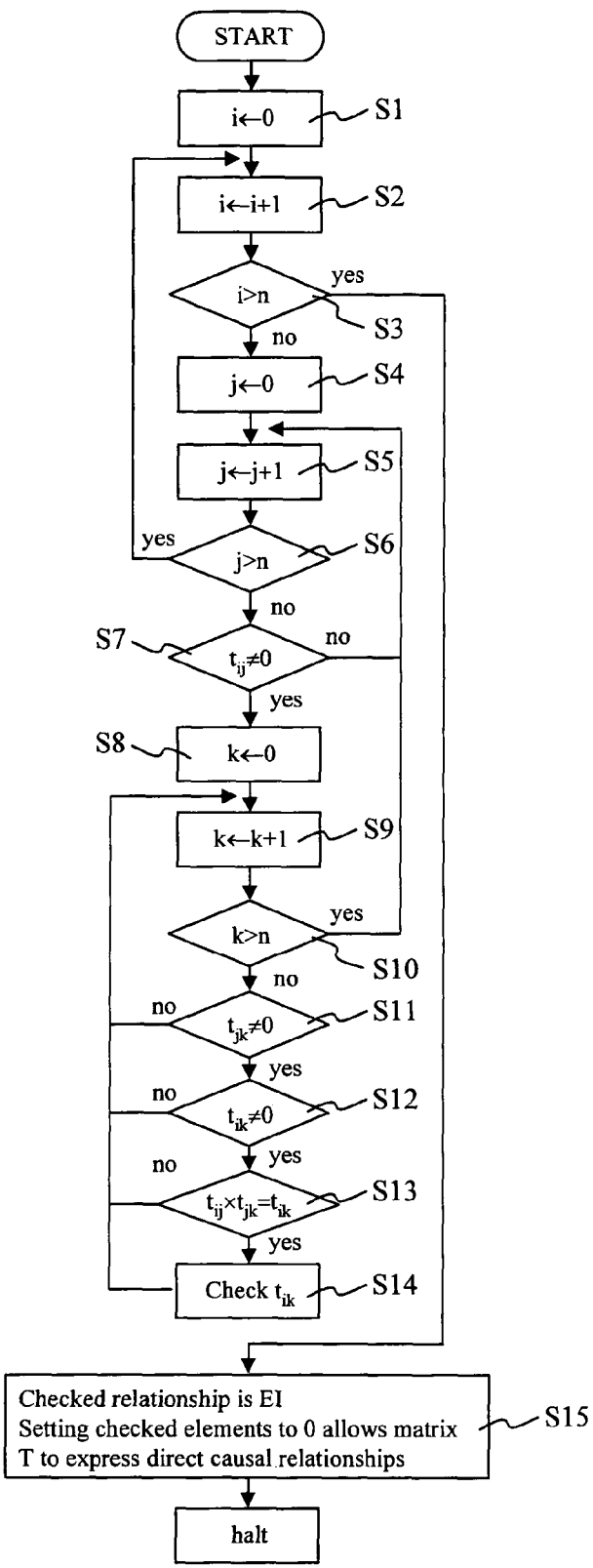
FIG. 13 is a diagram showing a flowchart that shows how a program for retrieving indirect causal relationships from an original network is executed.

FIG. 13 shows a flowchart showing how the modified Warshall's algorithm is executed. The steps shown in FIG. 13 are as described below. First, all the genes are sequentially numbered 1 to n (total number of genes), and a matrix that expresses the causal relationships constituting the original network is defined as T. Here, each of elements of T is defined as $t_{pq}$, which denotes the presence or absence of a causal relationship from the gene p to the gene p. If an activation causal relationship (positive causal relationship) is present, $t_{pq}=1$. If an inhibition causal relationship (negative causal relationship) is present, $t_{pq}=-1$. If no causal relationship is present, $t_{pq}=0$.

In FIG. 13, the process shown in S1 to S7 checks whether or not, for an index i=1 to n and an index j=1 to n, $t_{ij} \neq 0$, that is, a causal relationship from the gene i to the gene j is present. In FIG. 13, in the case that a causal relationship from the gene i to the gene j is present, the process shown in S8 to S11 checks whether or not, for an index k=1 to n, $t_{jk} \neq 0$, that is, a causal relationship from the gene j to the gene k is present. Moreover, if a causal relationship from the gene i to the gene k is present (process shown in S12 in FIG. 13) and $t_{ij} \times t_{jk} = t_{ik}$ (process shown in S13 in FIG. 13), $t_{jk}$ is checked (process shown in S14 in FIG. 13) because the causal relationship from the gene i to the gene k is indirect. The finally derived matrix enables the direct causal relationship and the indirect causal relationship to be distinguished from each other (process shown in S15 in FIG. 13).

The set of the indirect causal relationships retrieved by the indirect causal relationship retrieval engine is hereinafter referred to as EI. Accordingly, a set of direct causal relationships included in the original network is given by ET−EI and is hereinafter referred to as ES.

Figure 14:
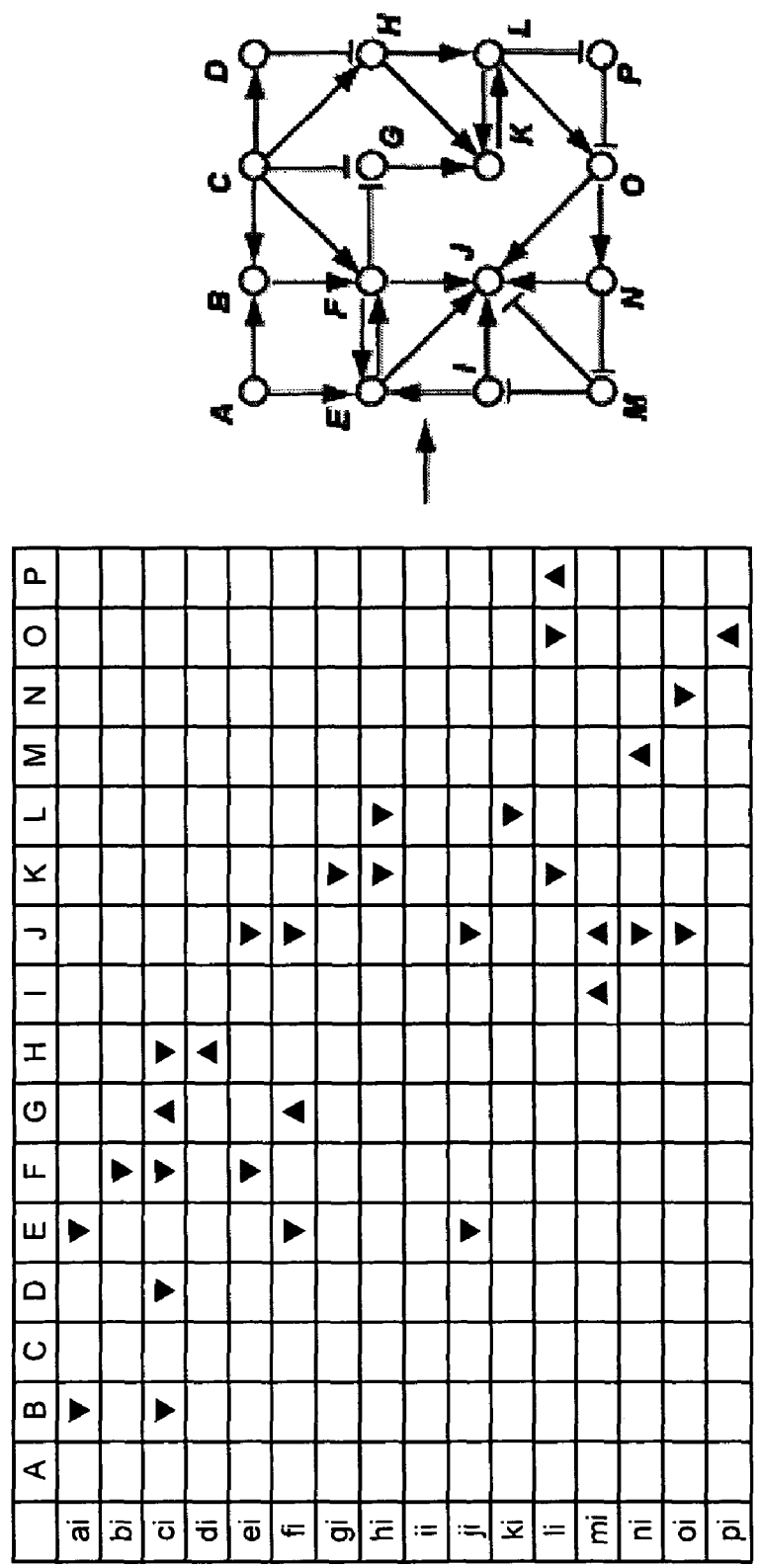
FIG. 14 is a diagram showing an original network containing causal relationships for 16 genes, genes A to P.
Figure 15:
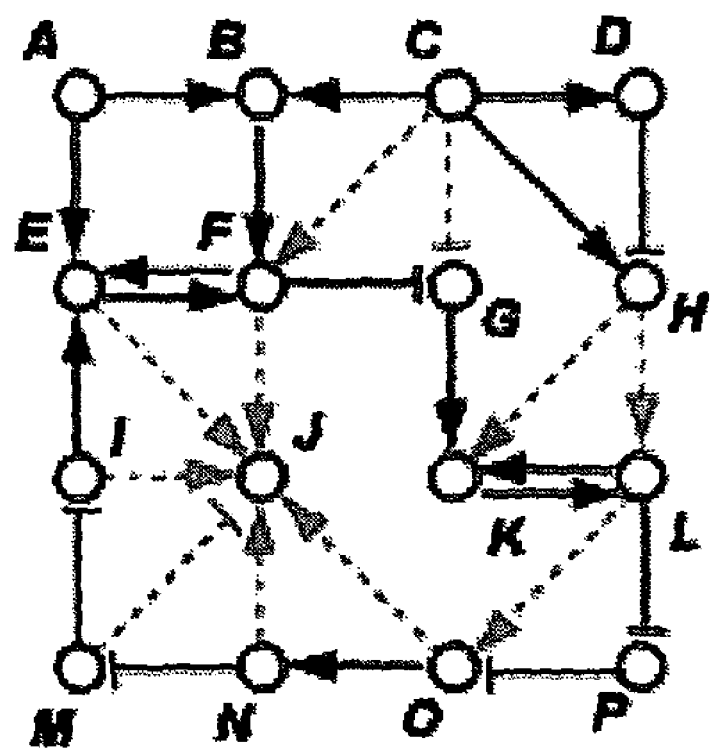
FIG. 15 is a diagram showing a gene network that shows the indirect causal relationships included in the original network shown in FIG. 14, as broken lines.

Here, by way of example, an original network is assumed which includes causal relationships for 16 genes, genes A to P, as shown in FIG. 14. The indirect causal relationship retrieval engine can predict a gene network comprising indirect causal relationships (shown by broken lines in FIG. 15) and direct causal relationships (shown by solid lines in FIG. 15) as shown in FIG. 15.

(ii) Explainable Indirect Causal Relationship Retrieval Engine

The explainable indirect causal relationship retrieval engine first retrieves indirect causal relationships whose presence can be explained on the basis of the direct causal relationships (ES), from the indirect causal relationships (EI) retrieved by the indirect causal relationship retrieval engine.

The indirect causal relationships whose presence can be explained on the basis of the direct causal relationships will be described, for convenience, with reference to the symbolic directed graph shown in FIG. 2. For the indirect causal relationship (broken line) corresponding to the positive control between the gene a and the gene b, when the direct causal relationship between the gene a and the gene c and the direct causal relationship between the gene c and the gene b contain an even number of negatively controlling causal relationships, the "indirect causal relationship in which the gene a positively controls the gene b" is defined as an "indirect causal relationship whose presence can be explained on the basis of a direct causal relationship". Further, as shown in FIG. 3, for the indirect causal relationship (broken line) in which the gene a negatively controls the gene b, when the direct causal relationship between the gene a and the gene c and the direct causal relationship between the gene c and the gene b contain an odd number of negatively controlling causal relationships, the "indirect causal relationship in which the gene a negatively controls the gene b" is defined as an "indirect causal relationship whose presence can be explained on the basis of a direct causal relationship".

For example, for the indirect causal relationships (broken lines) included in the gene network shown in FIG. 15, the causal relationship between a gene C and a gene F, the causal relationship between the gene C and a gene G, and the causal relationship between a gene L and a gene O are indirect causal relationships whose presence can be explained on the basis of the direct causal relationships.

The indirect causal relationships retrieved by the explainable indirect causal relationship retrieval engine are hereinafter referred to as EI*.

The explainable indirect causal relationship retrieval engine next retrieves indirect causal relationships whose presence can be explained on the basis of: indirect causal relationships whose presence can be explained on the basis of the direct causal relationships retrieved as described above; and/or direct causal relationships. In other words, in the gene network shown in FIG. 2 or 3, even if one or both of the causal relationship between the gene a and the gene c and the causal relationship between the gene c and the gene b are indirect causal relationships whose presence can be explained on the basis of the direct causal relationships retrieved as described above, when the genes a, b, and c are in the relationship as shown in FIG. 2 or 3, the indirect causal relationship between the gene a and the gene b is an indirect causal relationship whose presence can be explained on the basis of a direct causal relationship.

Figure 2:
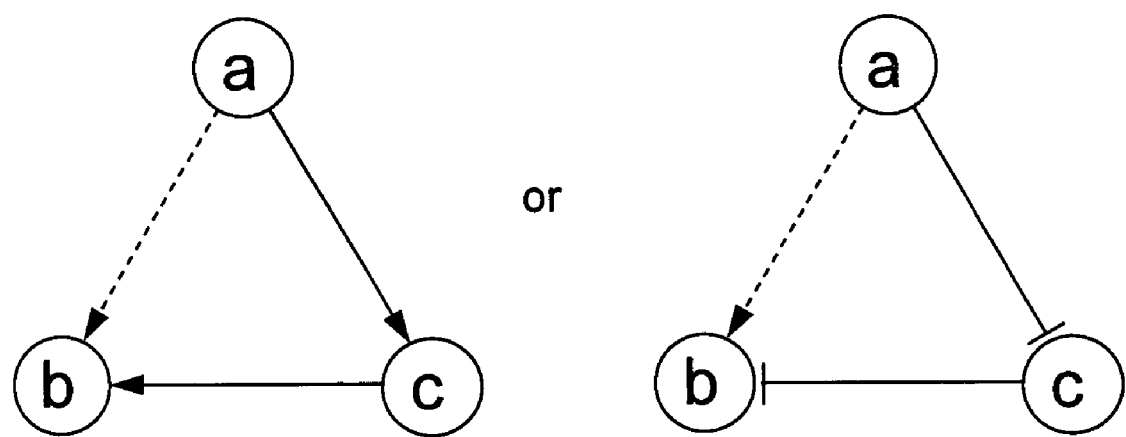
FIG. 2 is a diagram showing a symbolic directed graph illustrating a gene network comprising a gene a, a gene b, and a gene c and in which the gene a and the gene b have an indirect causal relationship that is a causal relationship in which the gene a positively controls the gene b.
Figure 3:
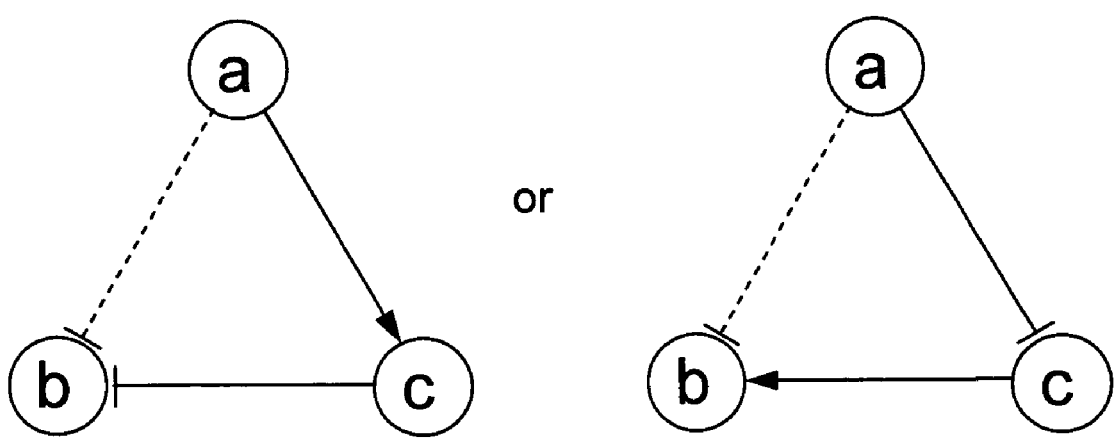
FIG. 3 is a diagram showing a symbolic directed graph illustrating a gene network comprising the genes a, b, and c and in which the genes a and b have an indirect causal relationship that is a causal relationship in which the gene a negatively controls the gene b.

That is, in the gene network shown in FIG. 2 or 3, when the causal relationship between the gene a and the gene c and the causal relationship between the gene c and the gene b are present in ES∪EI* and the genes a, b, and c are in the relationship as shown in FIG. 2 or 3, the indirect causal relationship between the gene a and the gene b is added to EI* as an indirect causal relationship whose the presence can be explained on the basis of a direct causal relationship. The explainable indirect causal relationship retrieval engine performs the above operation until there is no indirect causal relationship to be added to EI*.

Figure 16:
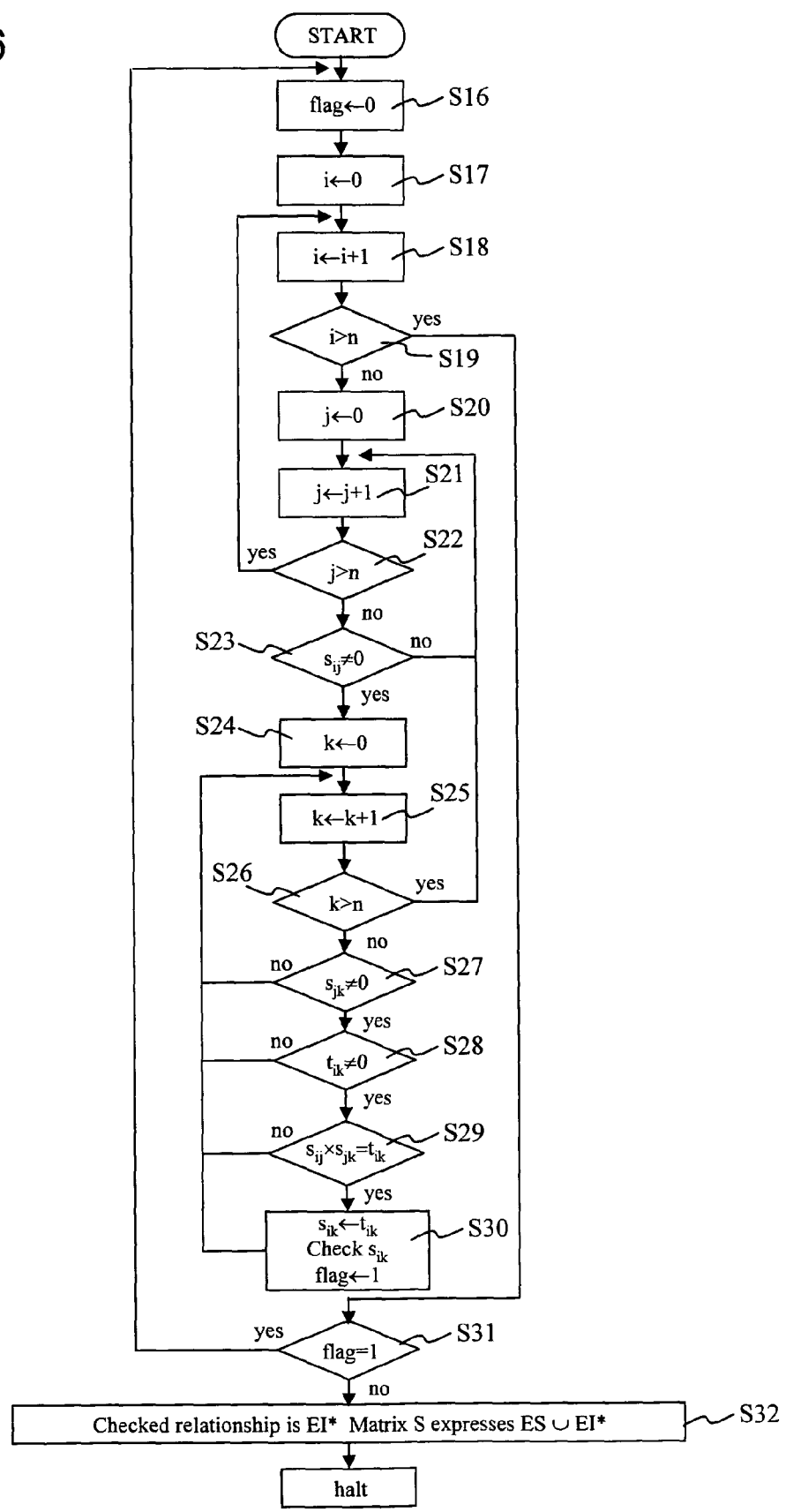
FIG. 16 is a diagram showing a flowchart that shows how an explainable indirect causal relationship retrieval engine is executed.

FIG. 16 shows a flowchart showing how the above algorithm is executed. The steps shown in FIG. 16 are as described below. A matrix expressing the causal relationships constituting the original network is defined as T. A matrix expressing the direct causal relationships is defined as S. Here, the elements of T and S are defined as $t_{pq}$ and $s_{pq}$, which denote the presence or absence of a causal relationship from the gene p to the gene p. If an activation causal relationship is present, $t_{pq}$, $s_{pq}$=1. If an inhibition causal relationship is present, $t_{pq}$, $s_{pq}$=−1. If no causal relationship is present, $t_{pq}$, $s_{pq}$=0.

The process shown in S16 to S30 in FIG. 16 searches for indirect causal relationships that are explainable on the basis of causal relationships present in S. This process uses a flag to check whether or not a new explainable indirect causal relationship has been detected among the indirect causal relationships (process shown in S31 in FIG. 16). If any such an indirect causal relationship is found, the process in S16 to S30 is repeated because this causal relationship may be used to explain other indirect causal relationships. When no new explainable indirect causal relationship is detected, the process shown in S16 to S30 in FIG. 16 is halted. The flowchart shown in FIG. 16 allows all the causal relationships included in EI* to be detected (process shown in S32 in FIG. 16).

The indirect causal relationships (EI*) detected by the explainable indirect causal relationship retrieval engine are explainable on the basis of the direct causal relationships and/or indirect causal relationships whose presence can be explained on the basis of the direct causal relationships. Accordingly, excluding these indirect causal relationships from the original network does not reduce the amount of information contained in the original network.

(iii) Minimum Number Relationship Retrieval Engine

The minimum number relationship retrieval engine executes information processing if there remains any indirect causal relationship (hereinafter referred to as an "unexplainable indirect causal relationship") after the indirect causal relationships (EI*) retrieved by the explainable indirect causal relationship retrieval engine are excluded from the indirect causal relationships (EI) retrieved by the indirect causal relationship retrieval engine (see FIG. 7). A set of unexplainable indirect causal relationships is hereinafter referred to as EN(=EI-EI*). That is, the minimum number relationship retrieval engine is means executed if ES∪EI*≠ET.

Specifically, in the gene network shown in FIG. 15, unexplainable indirect causal relationships (EN) correspond to the indirect causal relationships (broken lines) contained in this gene network and from which the causal relationship between the gene C and the gene F, the causal relationship between the gene C and the gene G, and the causal relationship between the gene L and the gene O are excluded.

The minimum number relationship retrieval engine retrieves a minimum number of indirect causal relationships that can explain the presence of all the indirect causal relationships, from the set (EN) of many unexplainable indirect causal relationships present in the gene network.

Specifically, the program for predicting a gene network according to the present invention preferably may allow the computer to function as (α) to (γ) means described below.

(α) Means for retrieving, from the set (EN) of the unexplainable indirect causal relationships corresponding to the indirect causal relationships (EI) from which the indirect causal relationships (EI*) retrieved by the explainable indirect causal relationship retrieval engine are excluded, indirect causal relationships that can explain none of the other unexplainable indirect causal relationships in cooperation with one of the causal relationships (ET) included in the original network (set of indirect causal relationships retrieved by the present means is hereinafter referred to as EN*), (β) Means for repeating a process of, for the set (EN) of the unexplainable indirect causal relationships from which the indirect causal relationships included in EN* are excluded, adding, to EN*, indirect causal relationships in the set (EN) which can explain only the other unexplainable indirect causal relationships included in EN* within EN, in cooperation with one of the causal relationships (ET) included in the original network, until there remains no indirect causal relationship to be added to EN*, (γ) Means for dividing a set (EN-EN*) of unexplainable indirect causal relationships not included in EN* detected by the (β) means into groups, and (δ) Means for retrieving a minimum number of indirect causal relationships for each of the groups formed by the (γ) means, on the basis of the indirect causal relationships included in the group.

(α) Means

Figure 17:
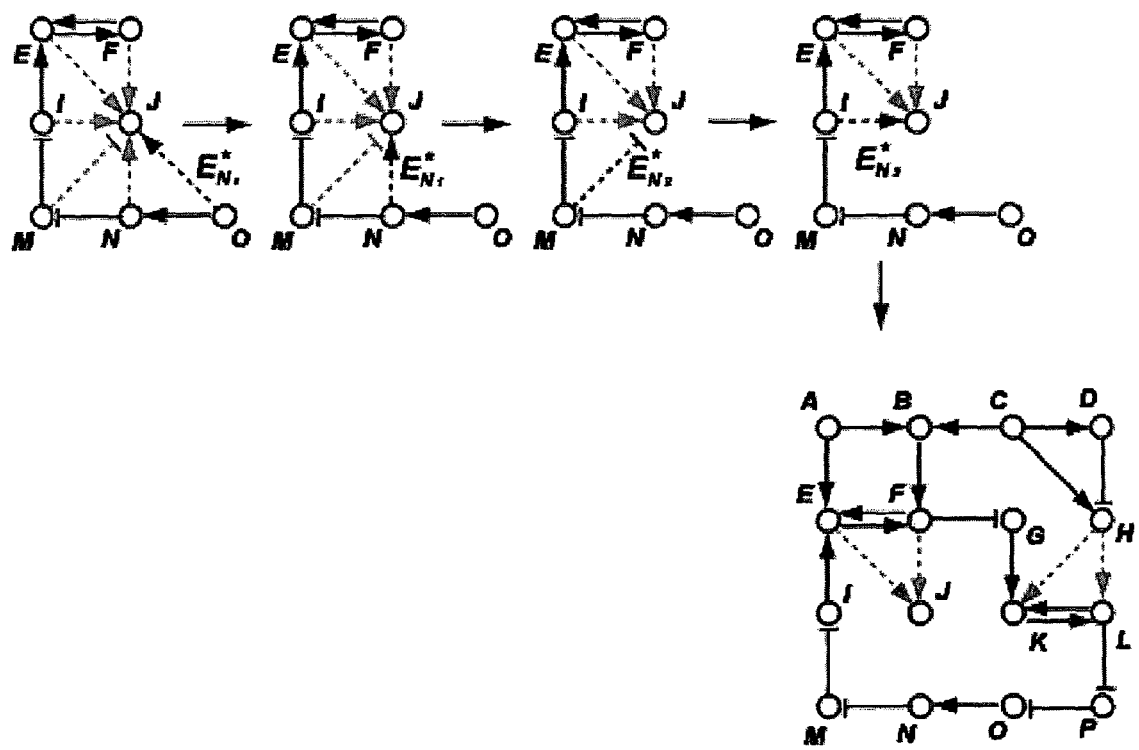
FIG. 17 is a diagram showing a symbolic directed graph illustrating a part of a process of a minimum number relationship retrieval engine which is a part of the gene network shown in FIG. 15.

Specifically, for a part of the gene network shown in FIG. 17 (part of the gene network shown in FIG. 15), the (α) means defines the indirect causal relationship ($E_{N0}$*) between the gene O and the gene J as EN*.

(β) Means

In a part of the gene network shown in FIG. 17 (part of the gene network shown in FIG. 15), the indirect causal relationship ($E_{N1}$*) between the gene N and the gene J can explain only the indirect causal relationship ($E_{N0}$*) between the gene O and the gene J which is included in EN* within EN, in cooperation with the direct causal relationship (ET) between the gene O and the gene N. Accordingly, the (β) means adds the indirect causal relationship ($E_{N1}$*) between the gene N and the gene J to EN*. Similarly, for a part of the gene network shown in FIG. 17, the (β) means adds the indirect causal relationship ($E_{N2}$*) between the gene M and the gene J and the indirect causal relationship ($E_{N3}$*) between the gene I and the gene J, to EN*.

(γ) Means

The (γ) means first adds one of the indirect causal relationships included in EN-EN* to an empty group. The (γ) means then adds other indirect causal relationships included in EN-EN* and which are in a relationship (A) or (B) defined below, to this group.

(A) If one of the indirect causal relationships included in the group and one of the causal relationships included in ET can explain a predetermined indirect causal relationship included in EN-EN*, the predetermined indirect causal relationship is added to the group.

(B) If one or both of a pair of causal relationships included in ET and which can explain one of the indirect causal relationships included in the group are indirect causal relationship included in EN-EN*, the indirect causal relationship included in EN-EN* are added to the group.

The (γ) means then further adds indirect causal relationships included in EN-EN* and which are in the relationship (A) or (B) to the group. The (γ) means repeats this process until there remains no indirect causal relationship to be added.

The (γ) means then defines one of the indirect causal relationship included in EN-EN* and which has not been added to the group, as another new group and executes a similar process on this group. The (γ) means repeats creating a new group until EN-EN* includes no indirect causal relationship. Thus, the (γ) means can divide the indirect causal relationships included in EN-EN* into a plurality of groups on the basis of the indirect causal relationships (EN*) retrieved by the (β) means. The process by the (γ) means may result in the formation of only one group.

Figure 18:
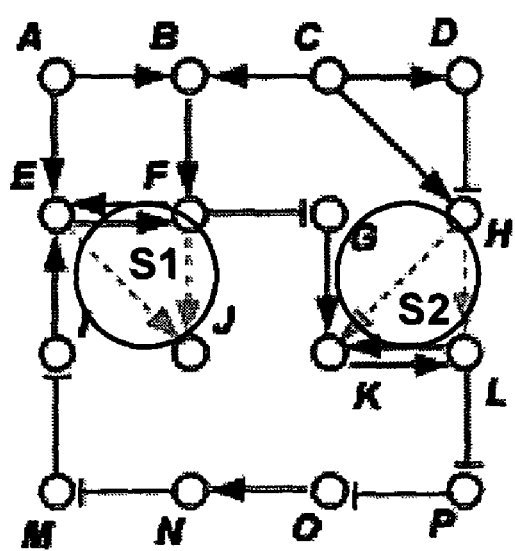
FIG. 18 is a diagram showing, as a symbolic directed graph, the gene network shown in FIG. 15 and in which a set (EN-EN*) of unexplainable indirect causal relationships has been divided into groups.
Figure 18:
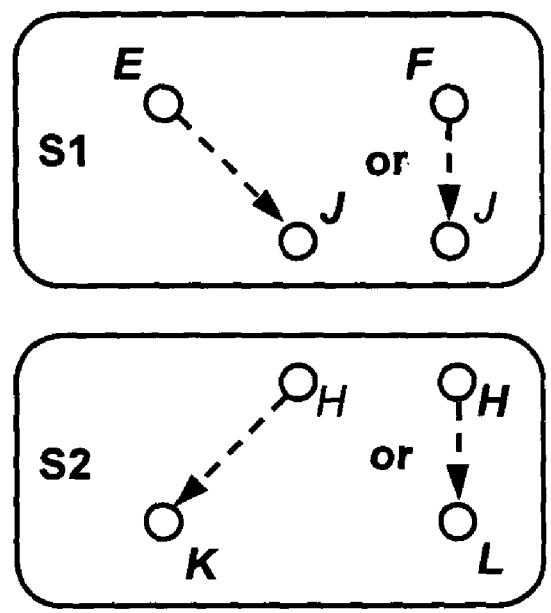

For example, the gene network shown in FIG. 15 is expressed as a gene network comprising only the direct causal relationships (ES) and the indirect causal relationships included in EN-EN* as shown in FIG. 18. The (γ) means divides the indirect causal relationships into two groups shown as "S1" and "S2" in FIG. 18.

(δ) Means

For each of the groups formed by the (γ) means, the (δ) means detects, in the indirect causal relationships included in the group, a minimum number of indirect causal relationships required to explain all the indirect causal relationships included in the group in cooperation with the causal relationships included in ES∪EI*.

Specifically, the (δ) means first executes the following process on all the indirect causal relationships included in the group: retrieving one indirect causal relationship from the subject group and determining whether or not this indirect causal relationship can explain all the indirect causal relationships included in the group in collaboration with the causal relationships included in ES ∪ EI*. The (δ) means detects all the explainable indirect causal relationships as a "minimum number of indirect causal relationships".

If the retrieved indirect causal relationship cannot explain all the indirect causal relationships included in the group, the (δ) means executes the following process on all possible combinations of the indirect causal relationships included in the group: retrieving a combination of two indirect causal relationships from the subject group and determining whether or not the two indirect causal relationships and the causal relationships included in ES∪EI* can explain all the indirect causal relationships included in the group. Further, if none of combinations of two indirect causal relationships can explain the indirect causal relationships included in the group, the number of indirect causal relationships in the combination is sequentially incremented by one and a similar process is executed. The (δ) means detects all the combinations of explainable indirect causal relationships as a "minimum number of indirect causal relationships".

Specifically, the minimum number relationship retrieval engine retrieves the indirect causal relationship between the gene E and the gene J or the indirect causal relationship between the gene F and the gene J from the S1 group shown in FIG. 18, as a minimum number of indirect causal relationships. The minimum number relationship retrieval engine retrieves the indirect causal relationship between the gene H and the gene K or the indirect causal relationship between the gene H and the gene L from the S2 group as a minimum number of indirect causal relationships.

Figure 19:
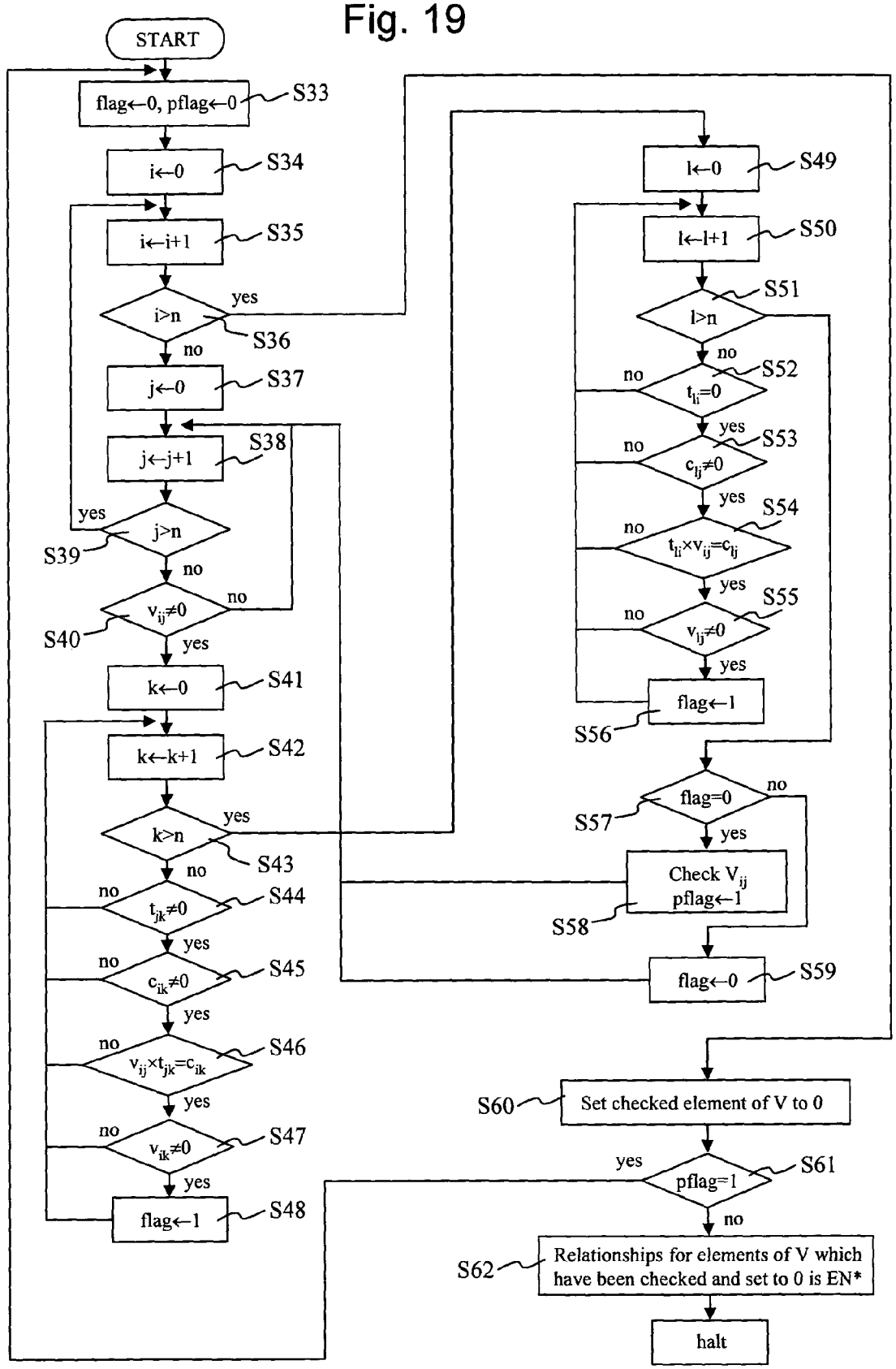
FIG. 19 is a diagram showing a flowchart that shows how (α) means and (β) means of the minimum number relationship retrieval engine are executed.

FIG. 19 shows a flowchart showing how the (α) and (β) means of the above algorithm are executed. The steps shown in FIG. 19 are as described below. A matrix expressing the causal relationships constituting the original network is defined as T. A matrix expressing the indirect causal relationships is defined as C. A matrix expressing the unexplainable indirect causal relationships is defined as V. Here, the elements of T, C, and V are defined as $t_{pq}$, $c_{pq}$, and $v_{pq}$ which denote the presence or absence of a causal relationship from the gene p to the gene p. If an activation causal relationship is present, $t_{pq}$, $c_{pq}$, $v_{pq}$=1. If an inhibition causal relationship is present, $t_{pq}$, $c_{pq}$, $v_{pq}$=−1. If no causal relationship is present, $t_{pq}$, $c_{pq}$, $v_{pq}$=0.

First, the processes shown in S33 to S40 in FIG. 19 detect elements such that $v_{ij}$≠0 in V, that is, retrieves one of the causal relationships in EN. The processes shown in S41 to S48 and in S49 to S56 in FIG. 19 determine whether or not the retrieved causal relationship explains the causal relationships included in another EN in cooperation with one of the causal relationships in ET. If the retrieved causal relationship explains the causal relationships included in another EN, the flag is set to 1. Otherwise the flag is set to 0 (processes shown in S48 to S56 in FIG. 19). After determinations are executed on the causal relationships included in all ETs, if the retrieved causal relationship does not explain any causal relationships included in the other ENs, the causal relationship retrieved from EN is checked (process shown in S58 in FIG. 19). After the above search is executed on all the elements of V that are $v_{ij} \neq 0$, the checked elements are set to 0 (process shown in S60 in FIG. 19). If any newly checked causal relationship is present, the above process is repeated until there is no causal relationship to be newly checked (process shown in S61 in FIG. 19). The causal relationships checked on the first turn of the process are $EN^*_{n0}$. The causal relationships checked on the x-th and subsequent turns are $EN^*_{n(x-1)}$ (process shown in S62 in FIG. 19)

Figure 20:
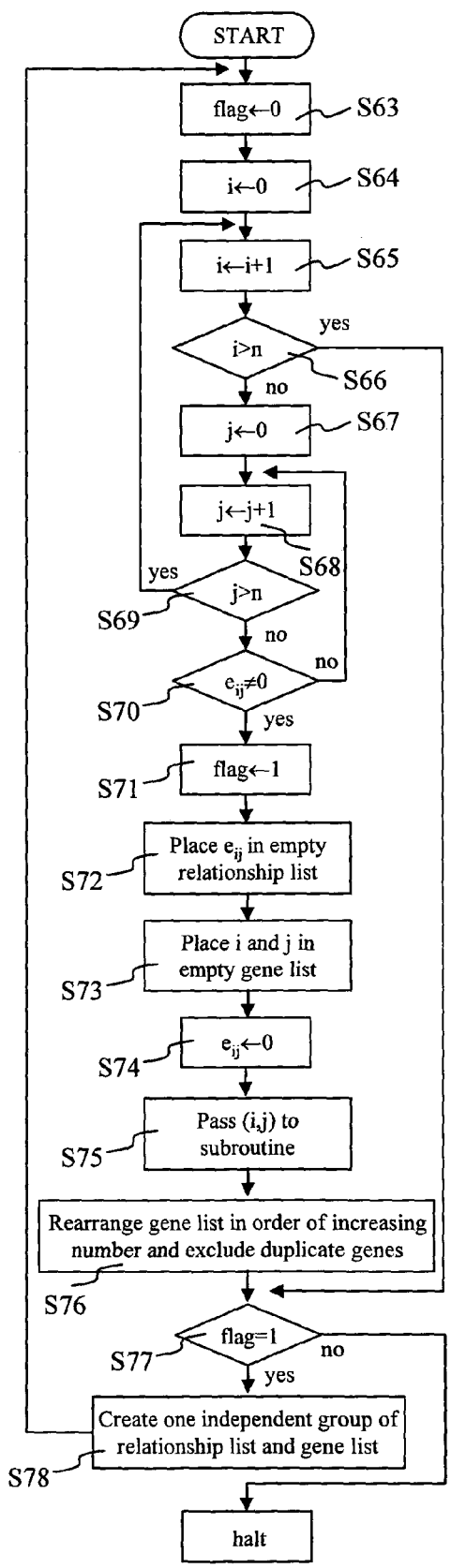
FIG. 20 is a diagram showing a flowchart that shows how (γ) means of the minimum number relationship retrieval engine is executed.

FIG. 20 shows a flowchart showing how the (γ) means of the above algorithm is executed. The steps shown in FIG. 20 are as described below. A matrix expressing the causal relationships constituting the original network is defined as T. A matrix expressing the causal relationships included in EN-EN* is defined as E. Here, the elements of T and E are defined as $t_{pq}$ and $e_{pq}$ which denote the presence or absence of a causal relationship from the gene p to the gene p. If an activation causal relationship is present, $t_{pq}$, $e_{pq}$=1. If an inhibition causal relationship is present, $t_{pq}$, $e_{pq}$=-1. If no causal relationship is present, $t_{pq}$, $e_{pq}$=0.

First, the processes shown in S63 to S70 in FIG. 20 detects elements of E which are $e_{ij} \neq 0$, that is, retrieves one of the causal relationships included in EN-EN*. Then, the process shown in S72 in FIG. 20 adds the causal relationship retrieved in S70 to an empty relationship list. Further, the process shown in S73 in FIG. 20 adds each of a pair of genes constituting the causal relationship retrieved in S70 to an empty gene list. This gene list is required for the subsequent process (δ) means.

Then, the process shown in S74 in FIG. 20 sets $e_{ij}$ to 0, that is, deletes the causal relationship with $e_{ij}$ from EN-EN*. The process shown in S75 in FIG. 20 places i and j in a subroutine 1 that searches for all of those causal relationships included in EN-EN* which belong to the same group as that to which the causal relationship retrieved in S70 belongs. The process shown in S76 in FIG. 20 then rearranges a gene list constituting all the causal relationships retrieved by the subroutine 1, in order of increasing number. The process shown in S76 in FIG. 20 then excludes duplicate genes.

The (γ) means checks whether or not all the elements of E are zero, that is, whether or not EN-EN* is empty (process shown in S77 in FIG. 20). If EN-EN* is not empty ("yes" in the process shown in S77 in FIG. 20), then the process shown in S78 in FIG. 20 creates a group of a relationship list and a gene list. The above process is then similarly repeated (processes shown in S63 to S77 in FIG. 20). If EN-EN* is empty ("no" in the process shown in S77 in FIG. 20), then the process is terminated because all the causal relationships included in EN-EN* have been divided into groups.

Figure 21:
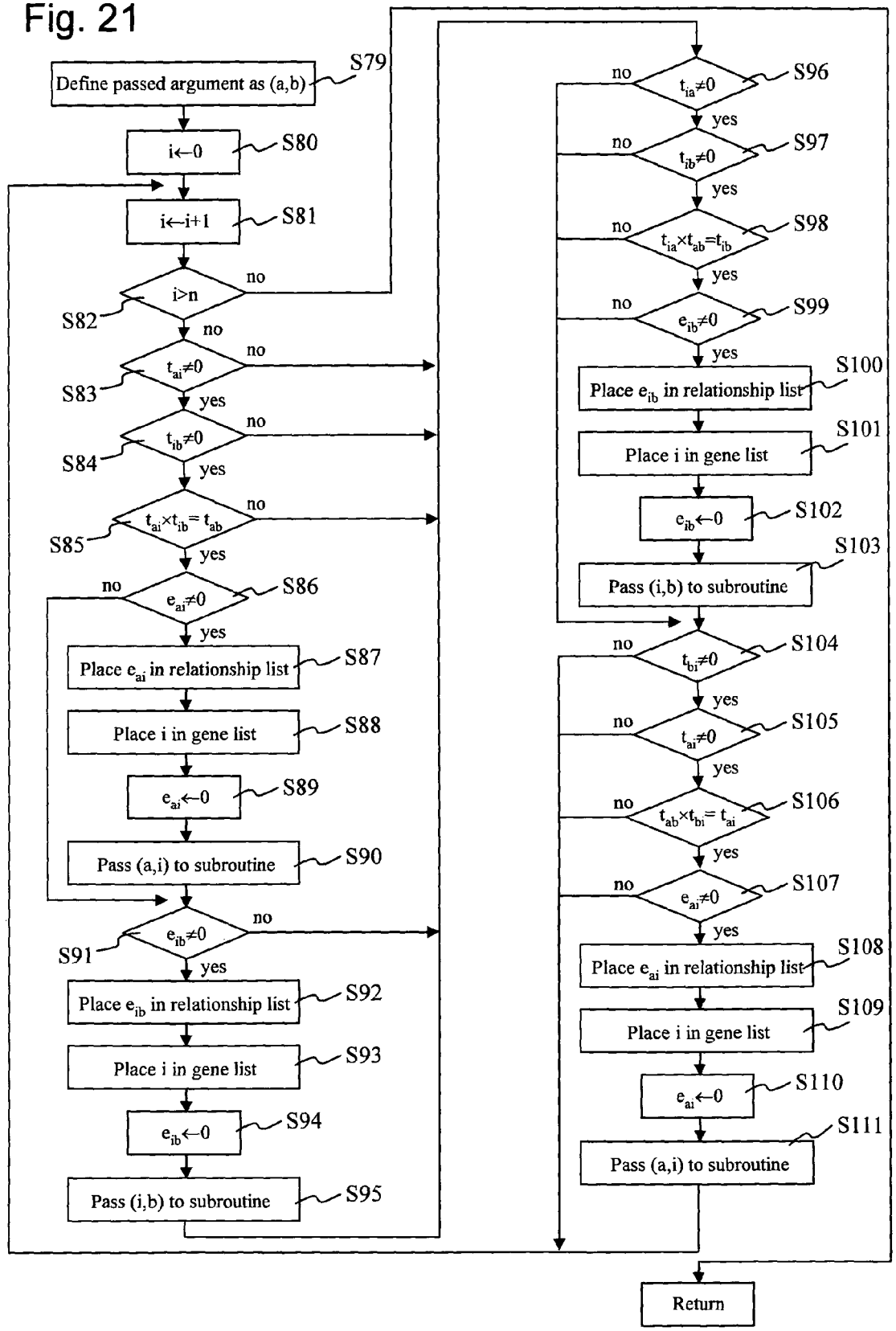
FIG. 21 is a diagram showing a flowchart of a subroutine 1 that is executed in the process shown at S75 in FIG. 20.

FIG. 21 shows a flowchart showing how the subroutine 1 of the (γ) means is executed. The steps shown in FIG. 21 are as described below. First, the processes shown in S79 to S85 in FIG. 21 retrieves causal relationships $t_{ai}$ and $t_{ib}$ using (a, b) as an argument passed to the subroutine 1. The present subroutine first executes a process corresponding to (B) of the (γ) means (processes shown in S86 to S95 in FIG. 21). If neither $e_{ai}$ nor $e_{ib}$ is zero, the processes shown in S86 to S95 in FIG. 21 places $e_{ai}$ and $e_{ib}$ in the relationship list and i in the gene list.

Then, a process corresponding to (A) of the (γ) means is executed (processes shown in S96 to S103 in FIG. 21 and processes shown in S104 to S111 in FIG. 21). Here, the process corresponding to (A) can be executed in two manners. That is, one of the manners is used if for the two causal relationships that explain the indirect causal relationships included in EN-EN*, one of them, included in the group, precedes the other, included in ET (processes shown in S96 to S103 in FIG. 21). The other manner is used if the causal relationship included in ET precedes the causal relationship included in the group (processes shown in S104 to S111 in FIG. 21).

If $e_{ib}$ is not 0 in the processes shown in S96 to S103 in FIG. 21 or if $e_{ai}$ is not 0 in the processes shown in S104 to S111 in FIG. 21, $e_{ai}$ and $e_{ib}$ are placed in the relationship list, with i placed in the gene list.

Further, the present subroutine 1 executes processes corresponding to (A) and (B) of the (γ) means on the causal relationships newly added to the relationship list in the processes shown in S86 to S95 in FIG. 21, in the processes shown in S96 to S103 in FIG. 21, and in the processes shown in S104 to S111 in FIG. 21. The present subroutine 1 is thus nested.

Figure 22:
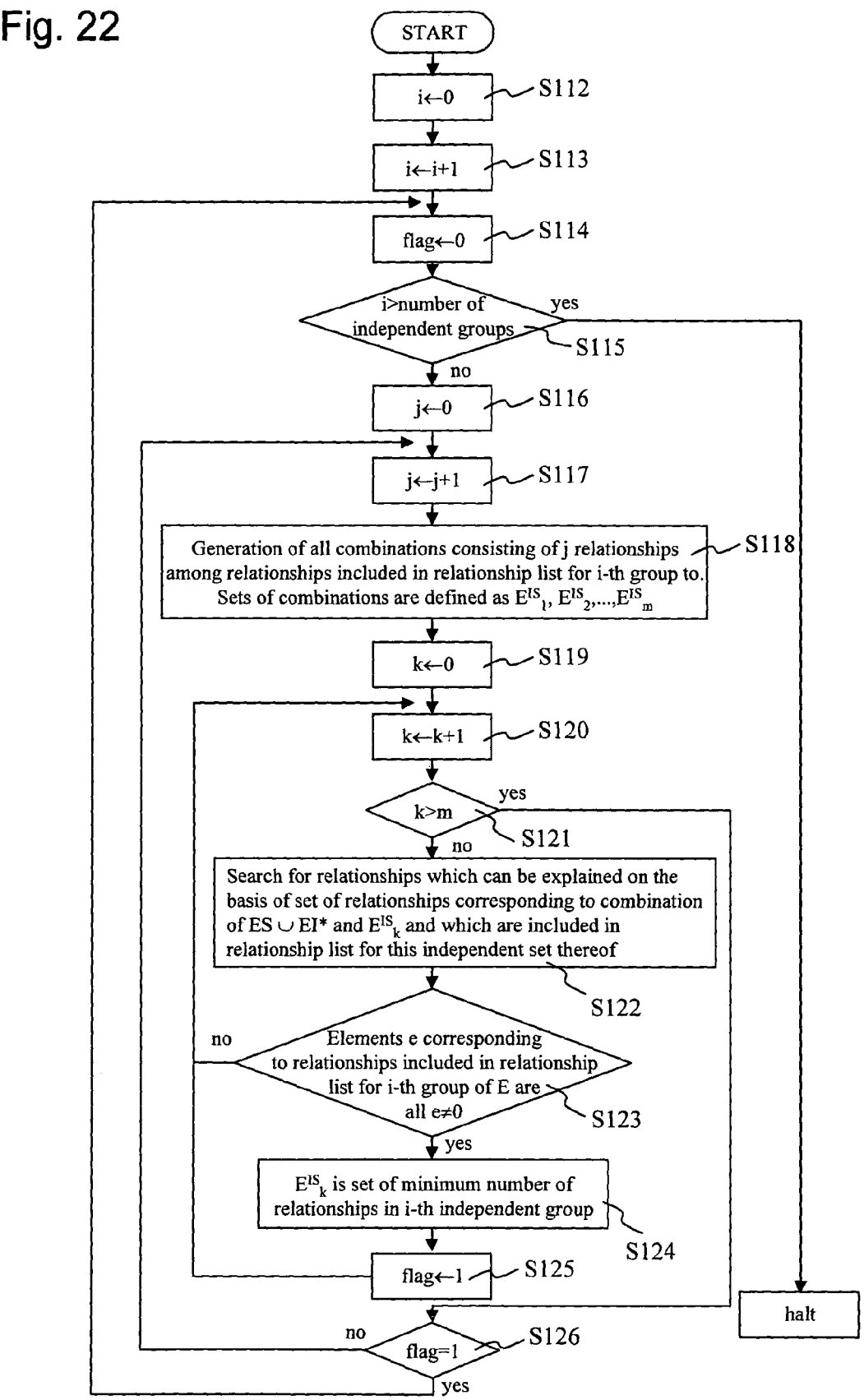
FIG. 22 is a diagram showing a flowchart that shows how (δ) means of the minimum number relationship retrieval engine is executed.

FIG. 22 shows a flowchart showing how the (δ) means of the algorithm is executed. The steps shown in FIG. 22 are as described below. To search all the groups for a set of causal relationships included in such a minimum number relationship list as explains all the causal relationships included in the relationship list for each group, in cooperation with ESUEI*, an index i is used to execute the process described below a number of times equal to the number of groups.

That is, first, the processes shown in S112 to S118 in FIG. 22 generate a combination comprising j relationships from the relationship list for the group. Then, the processes shown in S119 to S122 in FIG. 22 detects causal relationships included in the relationship list for the group and which are explainable on the basis of $ESUEI^*UE^{IS}_k$. The process shown in S122 is executed in accordance with the flowchart shown in FIG. 23 and will be described below in detail.

Then, the process shown in S123 in FIG. 22 checks whether or not all the causal relationships included in the relationship list for the group have been explained. If all these causal relationships have been successfully explained ("yes" in the process shown in S123), the process proceeds to S124 in FIG. 22. Otherwise ("no" in the process shown in S123) a different combination is added to ESUEI*, and the processes in S120 to S123 are similarly executed. In S124 in FIG. 22, $E^{IS}_k$ is stored as a set of causal relationships included in such a minimum number relationship list as explains all the causal relationships included in the relationship list for each group, in cooperation with ESUEI*. In S125 in FIG. 22, if such a set is found, the flag is set to 1, and otherwise the flag is set to 0. In S126 in FIG. 22, if no such a set is found (flag=0), a combination comprising one more relationships is generated (processes shown in S117 and S118 in FIG. 22). The processes shown in S119 to S125 are then repeated.

Figure 23:
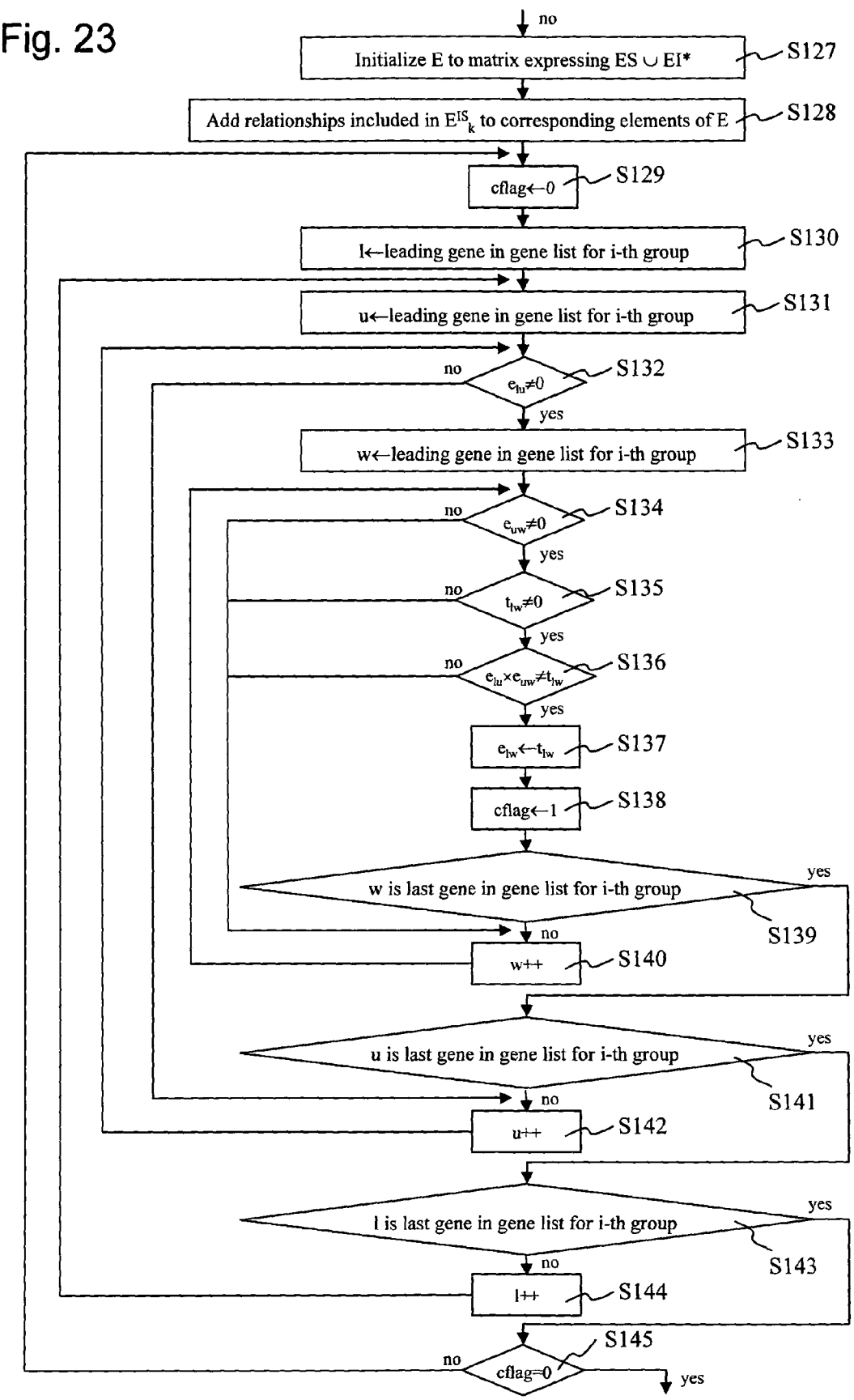
FIG. 23 is a diagram showing a flowchart of the process shown in S122 in FIG. 20.

FIG. 23 shows a flowchart showing how the (δ) means executes the process shown in S122. The steps shown in FIG. 23 are as described below. E is initialized to the matrix expressing ESUEI* (process shown in S127 in FIG. 23). The causal relationships included in $E^{IS}_k$ are then added to E as its elements (process shown in S128 in FIG. 23). The processes shown in S129 to S144 in FIG. 23 searches the relationship list for other causal relationships that can be explained by the causal relationship present in E. That is, if the causal relationship from the gene l to the gene u, which are set in S130 and S131 in FIG. 23, is present in E ("yes" in S132), the causal relationship from the gene u to the gene w, set in S133, is present in E ("yes" in S134), and the causal relationship from the gene l to the gene w is present in T and can be explained by the above two causal relationships ("yes" in S135 and S136), then information indicating that the causal relationship from the gene l to the gene w can be explained is saved (process shown in S137 in FIG. 23). In S140, S142, and S144, "w++", "u++", and "l++" mean a gene next to a gene list included in the i-th group.

If any new explainable causal relationship is found, then this causal relationship may be used to newly explain causal relationships included in the relationship list. Thus, the process shown in S145 in FIG. 23 prepares a cflag and the appropriate process is repeated until there is no explainable causal relationship.

As described above, the minimum number relationship retrieval engine can retrieve a minimum number of indirect causal relationships required to explain the presence of all the indirect causal relationships included in the original network, in cooperation with direct causal relationships. In other words, gene expression data or the like, on which the original network is based, can be reproduced by using the indirect causal relationships retrieved by the minimum number relationship retrieval engine, and the direct causal relationships.

(iv) Prediction Engine

The prediction engine predicts a gene network by adding a minimum number of indirect causal relationships retrieved by the minimum number relationship retrieval engine, to the set (ES) of the direct causal relationships. In this case, if the minimum number relationship retrieval engine retrieves a plurality of indirect causal relationships or their combination as a minimum number of indirect causal relationships, the prediction engine predicts a plurality of gene networks.

Further, if the minimum number relationship retrieval engine retrieves a minimum number of indirect causal relationships for each of a plurality of groups, the prediction engine predicts a plurality of gene networks as a combination of the minimum numbers of indirect causal relationships retrieved for the respective groups.

Figure 24:
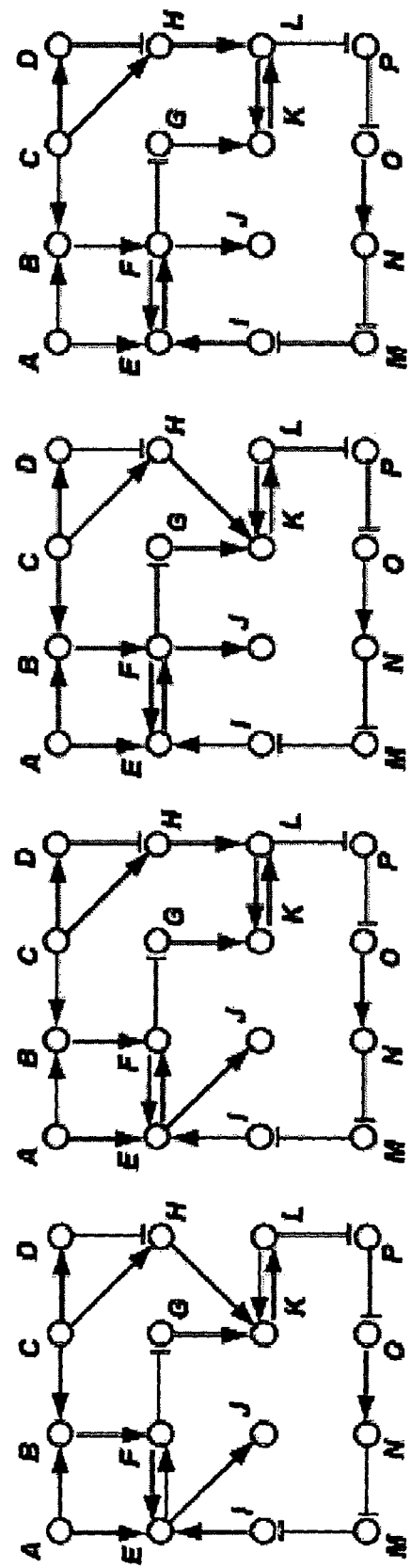
FIG. 24 is a diagram showing a gene network obtained via the prediction program according to the present invention, as a symbolic directed graph.

Specifically, if the minimum number relationship retrieval engine retrieves the indirect causal relationship between the gene E and the gene J or between the gene F and the gene J as a minimum number of indirect causal relationships for the S1 group and retrieves the indirect causal relationship between the gene H and the gene K or between the gene H and the gene L as a minimum number of indirect causal relationships for the S2 group as shown in FIG. 18, then the prediction engine predicts four types of gene networks as shown in FIG. 24.

Figure 25:
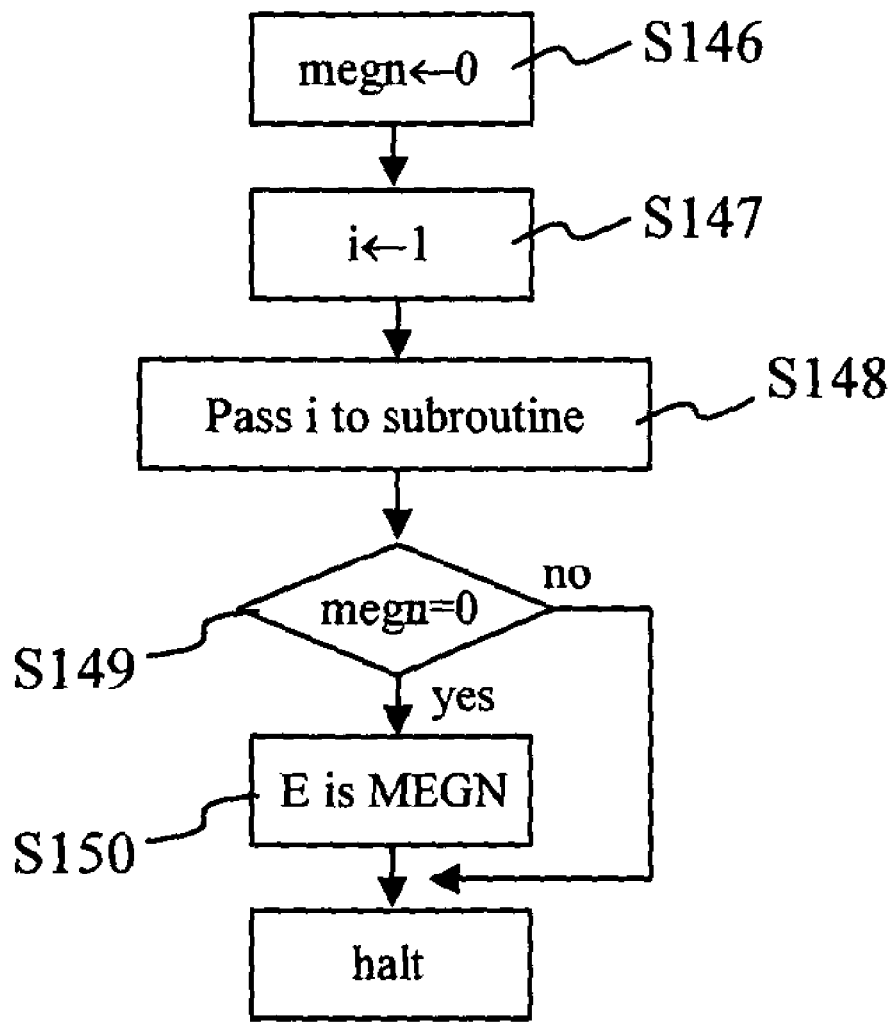
FIG. 25 is a diagram showing a flowchart that shows how a process of a prediction engine is executed.

FIG. 25 shows a flowchart that shows how the prediction engine is executed. The steps shown in FIG. 25 are as described below. A subroutine 2 is started which derives MEGN by adding, to ES, sets each of such a minimum number of indirect causal relationships as explain all the causal relationships included in the relationship list for the group, in cooperation with ESUEI*; one set of a minimum number of indirect causal relationships is obtained from each group (processes shown in S146 to S148 in FIG. 25). The process shown in S149 in FIG. 25 checks whether or not all the causal relationships constituting the original network can be explained by direct causal relationships. The process shown in S150 in FIG. 25 is executed if all the causal relationships are explainable.

Figure 26:
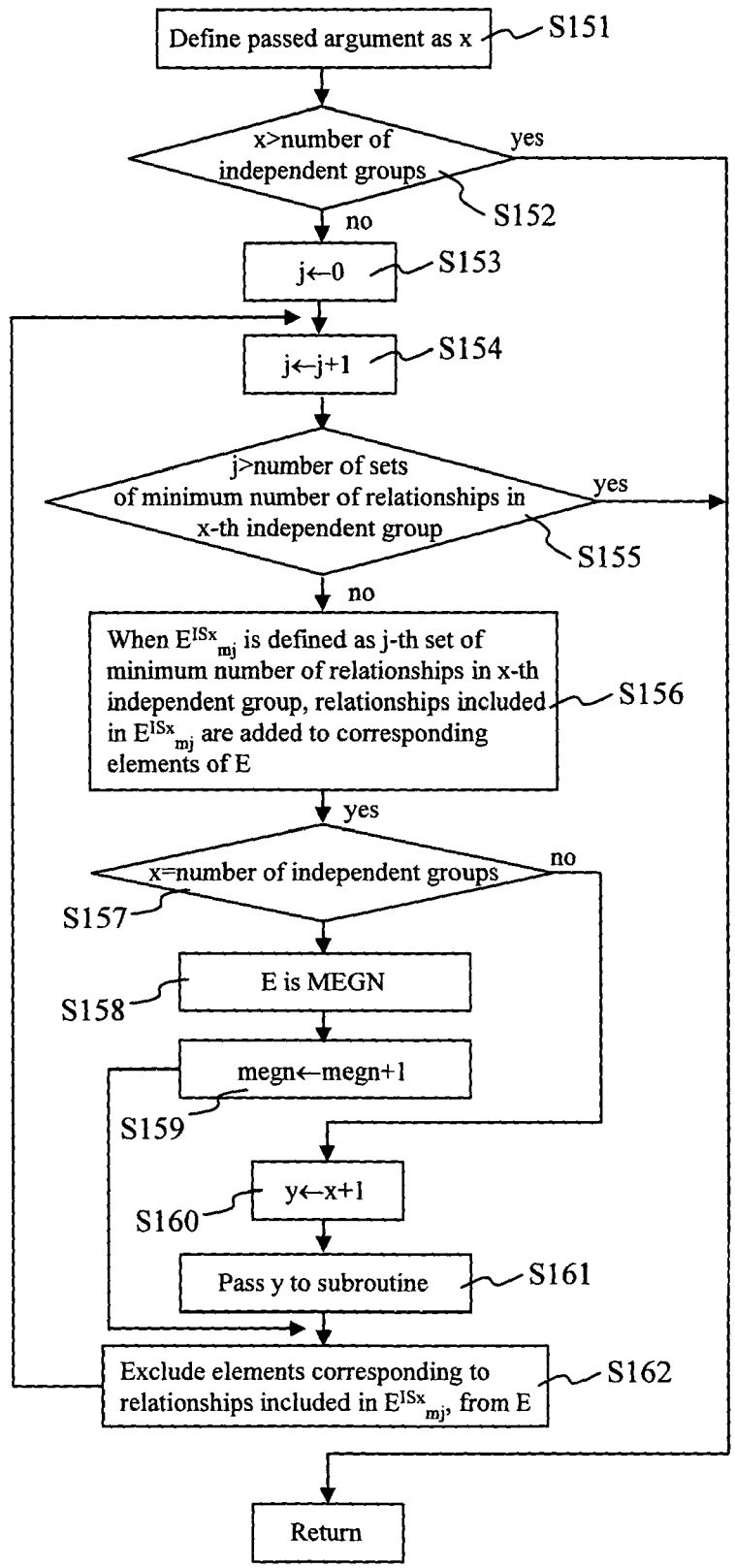
FIG. 26 is a diagram showing a flowchart of a subroutine 2 that is executed in the process shown in S148 in FIG. 25.

FIG. 26 shows a flowchart showing how the subroutine 2 of the prediction engine is executed. The steps shown in FIG. 26 are as described below. In S154 to S161 in FIG. 26, MEGN (minimum number of causal relationships) is derived by retrieving, from each group, a set of a minimum number of such indirect causal relationships as explain all the causal relationships included in the group, in cooperation with ESUEI* and adding the set to ES. In S157 and S158, included in S154 to S161, the process checks whether or not one set of relations from each group has been added to ES. If one set of relations from each group has been added to ES, ES is stored as MEGN.

The present program predicts a gene network composed of the direct causal relationships and a minimum number of indirect causal relationships. The predicted gene network can completely explain the original network predicted from gene expression data, on the basis of the direct causal relationships and minimum number of indirect causal relationships included in the gene network.

Therefore, the present program can predict a gene network that prevents the loss of an amount of information contained in the gene expression data on which the original network is based.

The gene network provided by the present prediction program can be output to the output means 106 such as a display in the form of, for example, a symbolic directed graph. Further, the gene network obtained can output the direct causal relationships and minimum number of indirect causal relationships included in the gene network, as numerical values.

All publications, patents, and patent applications cited herein are incorporated herein in their entity.

The invention claimed is:

1. A computer-implemented method of predicting a gene network comprising indirect causal relationships and direct causal relationship, in which a control relationship between a pair of genes is defined as a causal relationship and the causal relationship between the pair of genes is defined as a direct causal relationship if the pair of genes does not have a further causal relationship with another common gene, and in which the causal relationship between the pair of genes is defined as a direct causal relationship if the pair of genes has a further causal relationship with another common gene and if the presence of the causal relationship between the pair of genes cannot be explained by the causal relationship between the pair of genes and the another gene, and in which the causal relationship between the pair of genes is defined as an indirect causal relationship if the pair of genes has a further causal relationship with another common gene and if the presence of the causal relationship between the pair of genes can be explained by the causal relationship between the pair of genes and the another gene, the method comprising:

a step A of, using one or more computer processors, retrieving indirect causal relationships from a set of causal relationships relating to at least three genes and storing the indirect causal relationships on a computer memory;

a step B of 1): retrieving, using the one or more computer processors, from the indirect causal relationships retrieved in the step A, indirect causal relationships whose presence can be explained using the direct causal relationships, and subsequently 2): retrieving additional indirect casual relationships whose presence can be explained using: the indirect causal relationships whose presence can be explained using the direct causal relationships; and/or the direct causal relationships, wherein the retrieving of 2) is repeated using: the direct causal relationship; the indirect causal relationships whose presence can be explained using the direct causal relationships; and/or the additional indirect causal relationships until no new additional indirect causal relationships are detected;

a step C of retrieving, using the one or more computer processors, based on a set of indirect causal relationships that includes the indirect causal relationships retrieved and stored in the step A from which the indirect causal relationships retrieved in the step B are excluded, a minimum number of indirect causal relationships that can explain the presence of all the indirect causal relationships in cooperation with the direct causal relationships and the indirect causal relationships retrieved in the step B; and a step D of, using the one or more computer processors, excluding the indirect causal relationships from the set of causal relationships and adding the minimum number of indirect causal relationships retrieved in the step C to the resulting set of causal relationships to calculate a set of causal relationships, and predicting a gene network consisting of the calculated set of causal relationships.

2. The computer-implemented method of predicting a gene network according to claim 1, wherein in the step A, provided that when a causal relationship between a gene A and a gene B, a causal relationship between the gene A and a gene C, and a causal relationship between the gene C and the gene B is present among the gene A, the gene B and the gene C and the causal relationship between the gene A and the gene B is a positive causal relationship, the causal relationship between the gene A and the gene C and the causal relationship between the gene C and the gene B comprise an even number of negative causal relationships, or provided that when the causal relationship between the gene A and the gene B is a negative causal relationship, the causal relationship between the gene A and the gene C and the causal relationship between the gene C and the gene B comprise an odd number of negative causal relationships, the causal relationship between the gene A and the gene B is defined as an indirect causal relationship.

3. The computer-implemented method of predicting a gene network according to claim 1, wherein the step C includes:

a step C1 of defining the indirect causal relationships retrieved in the step A except the indirect causal relationships retrieved in the step B, as unexplainable indirect causal relationships, and retrieving, as minor unexplainable indirect causal relationships, those of the unexplainable indirect causal relationships which can explain none of the unexplainable indirect causal relationships in cooperation with one of the causal relationships included in the set of causal relationships on which the retrieval has been executed in the step A;

a step C2 of repeating a process of adding indirect causal relationships included in the unexplainable indirect causal relationships except the minor unexplainable indirect causal relationships to the set of minor unexplainable indirect causal relationships, wherein the added indirect causal relationships can explain only the minor unexplainable indirect causal relationships among the unexplainable indirect causal relationships in cooperation with one of the causal relationships included in the set of causal relationships on which the retrieval has been executed in the step A, until there remains no indirect causal relationships to be added;

a step C3 of dividing a set of unexplainable indirect causal relationships not included in the set of indirect causal relationships detected in the step C2, into groups; and a step C4 of retrieving a minimum number of indirect causal relationships for each of the groups formed in the step C3, on the basis of the indirect causal relationships included in the group.

4. The computer-implemented method of predicting a gene network according to claim 3, wherein in the step C3, the group division is carried out so that a minimum number of indirect causal relationships included in a particular group explains only the indirect causal relationships included in the group.

5. A program for predicting a gene network comprising indirect causal relationships and direct causal relationship stored on a non-transitory computer readable medium, in which a control relationship between a pair of genes is defined as a causal relationship and the causal relationship between the pair of genes is defined as a direct causal relationship if the pair of genes does not have a further causal relationship with another common gene, and in which the causal relationship between the pair of genes is defined as a direct causal relationship if the pair of genes has a further causal relationship with another common gene and if the presence of the causal relationship between the pair of genes cannot be explained by the causal relationship between the pair of genes and the another gene, and in which the causal relationship between the pair of genes is defined as an indirect causal relationship if the pair of genes has a further causal relationship with another common gene and if the presence of the causal relationship between the pair of genes can be explained by the causal relationship between the pair of genes and the another gene, the program, in estimating the gene network, allowing a computer to execute:

a step A of using retrieval means to retrieve indirect causal relationships from a set of data on causal relationships relating to at least three genes;

a step B of 1): using the retrieval means to retrieve, from the set of data on the indirect causal relationships retrieved in the step A, indirect causal relationships whose presence can be explained using the direct causal relationships, and subsequently 2): using the retrieval means to retrieve additional indirect casual relationships whose presence can be explained using: indirect causal relationships whose presence can be explained using a set of data on direct causal relationships; and/or the direct causal relationships, wherein the retrieving of 2) is repeated using: the direct causal relationships; the indirect causal relationships whose presence can be explained using the direct causal relationships; and/or the additional indirect causal relationships until no new additional indirect causal relationships are detected;

a step C of using the retrieval means to retrieve a minimum number of indirect causal relationships that can explain the presence of all the indirect causal relationships in cooperation with the direct causal relationships and the indirect causal relationships retrieved in the step B, from a set of data on indirect causal relationships calculated by using calculation means to exclude the data on the indirect causal relationships retrieved in the step B from the set of data on the indirect causal relationships retrieved in the step A; and a step D of using the calculation means to exclude the data on the indirect causal relationships from the set of data on causal relationships and using the calculation means to add the minimum number of indirect causal relationships retrieved in the step C to the resulting set of data on causal relationships to calculate a set of data on causal relationships, and using output means to output a gene network consisting of the calculated set of data on causal relationships.

6. The program for predicting a gene network according to claim 5, wherein in the step A, if the following condition is met: when a causal relationship between a gene A and a gene B, a causal relationship between the gene A and a gene C, and a causal relationship between the gene C and the gene B is present among the gene A, the gene B and the gene C and the causal relationship between the gene A and the gene B is a positive causal relationship, the causal relationship between the gene A and the gene C and the causal relationship between the gene C and the gene B contain an even number of negative causal relationships, or if the following condition is met: when the causal relationship between the gene A and the gene B is a negative causal relationship, the causal relationship between the gene A and the gene C and the causal relationship between the gene C and the gene B contain an odd number of negative causal relationships, the causal relationship between the gene A and the gene B is retrieved as an indirect causal relationship.

7. The program for predicting a gene network according to claim 5, wherein the step C includes:

a step C1 of defining the set of data on the indirect causal relationships retrieved in the step A from which the indirect causal relationships retrieved in the step B are excluded using the calculation means, as a set of data on unexplainable indirect causal relationships, and using the retrieval means to retrieve, from the resulting set of data on the unexplainable indirect causal relationships, indirect causal relationships that can explain none of the unexplainable indirect causal relationships in cooperation with one of the causal relationships included in the set of data on causal relationships on which the retrieval has been executed in the step A, as the minor unexplainable indirect causal relationship;

a step C2 of repeating a process of using the calculation means to add indirect causal relationships included in the unexplainable indirect causal relationships from which the minor unexplainable indirect causal relationships are excluded using the calculation means to the set of minor unexplainable indirect causal relationships, wherein the added indirect causal relationships can explain only the minor unexplainable indirect causal relationships among the unexplainable indirect causal relationships in cooperation with one of the causal relationships included in the set of causal relationships on which the retrieval has been executed in the step A using the retrieval means, until there remains no indirect causal relationships to be added;

a step C3 of using the calculation means to divide a set of data on unexplainable indirect causal relationships not included in the set of indirect causal relationships detected in the step C2, into groups; and a step C4 of using the retrieval means to retrieve a minimum number of indirect causal relationships for each of the groups formed in the step C3, on the basis of the indirect causal relationships included in the group.

8. The program for predicting a gene network according to claim 7, wherein in the step C3, the calculation means carries out the group division so that a minimum number of indirect causal relationships included in a particular group explains only the indirect causal relationships included in the group.

* * * * *